(12) United States Patent
Uchitani

(10) Patent No.: US 7,699,222 B2
(45) Date of Patent: Apr. 20, 2010

(54) DIAPER PRODUCT, SUPPLY INFORMATION MANAGEMENT SYSTEM, USAGE INFORMATION MANAGEMENT SYSTEM AND DIAPER PRODUCT MANAGEMENT SYSTEM

(75) Inventor: Koji Uchitani, Mima-gun (JP)

(73) Assignee: Livedo Corporation, Ehime (JP)

( * ) Notice: Subject to any disclaimer, the term of this patent is extended or adjusted under 35 U.S.C. 154(b) by 865 days.

(21) Appl. No.: 10/586,444

(22) PCT Filed: May 24, 2005

(86) PCT No.: PCT/JP2005/009441

§ 371 (c)(1),
(2), (4) Date: Jul. 18, 2006

(87) PCT Pub. No.: WO2005/115290

PCT Pub. Date: Dec. 8, 2005

(65) Prior Publication Data

US 2008/0110984 A1    May 15, 2008

(30) Foreign Application Priority Data

May 25, 2004   (JP)  ............................. 2004-154850
May 18, 2005   (JP)  ............................. 2005-145083

(51) Int. Cl.
*G06F 19/00*   (2006.01)
(52) U.S. Cl. ...................... 235/385; 235/375; 604/358
(58) Field of Classification Search .............. 235/385, 235/375; 340/573.1, 604; 604/358, 361
See application file for complete search history.

(56) References Cited

U.S. PATENT DOCUMENTS

| 5,838,240 | A  | * | 11/1998 | Johnson ...................... 340/604 |
| 6,714,121 | B1 |   | 3/2004  | Moore |
| 6,774,800 | B2 | * | 8/2004  | Friedman et al. ......... 340/573.5 |
| 7,188,748 | B2 | * | 3/2007  | Snell ........................... 221/192 |

(Continued)

FOREIGN PATENT DOCUMENTS

JP           3081774           8/2001

(Continued)

OTHER PUBLICATIONS

'Royal Network, Kaigo Kanren Shijo ni Sannyu—Nuno Omutsu o Cleaning', Nikkei Keizai Shimbun, Inc., Sep. 27, 2000, p. 13.

(Continued)

*Primary Examiner*—Ahshik Kim
(74) *Attorney, Agent, or Firm*—Wendroth, Lind & Ponack, L.L.P.

(57) ABSTRACT

A supply information management system comprises a reader/writer for writing process information on each of the processes to an IC tag and reading information out from the IC tag, the reader/writer being provided for a station for performing each of processes to supply a diaper product with an IC tag, and a host computer for receiving the information from the reader/writer. In the host computer, a product database which is a set of data elements each associating a serial number of an IC tag with process information thereof is stored and updated on the basis of the information from the reader/writer. The supply information management system makes it possible to specify an individual diaper product and perform a proper and easy management of information on supply of diaper products.

24 Claims, 32 Drawing Sheets

U.S. PATENT DOCUMENTS

| | | | |
|---|---|---|---|
| 2003/0158795 A1 | 8/2003 | Markham et al. | |
| 2004/0030309 A1* | 2/2004 | Huang | 604/361 |
| 2004/0103033 A1* | 5/2004 | Reade et al. | 705/16 |
| 2005/0148978 A1* | 7/2005 | Brumm et al. | 604/385.01 |
| 2008/0132859 A1* | 6/2008 | Pires | 604/361 |

FOREIGN PATENT DOCUMENTS

| | | |
|---|---|---|
| JP | 2002-73805 | 3/2002 |
| JP | 2002-123654 | 4/2002 |
| JP | 2002-150057 | 5/2002 |
| JP | 2002-324143 | 11/2002 |
| JP | 2003-58759 | 2/2003 |
| JP | 2003-141256 | 5/2003 |
| JP | 2003-182849 | 7/2003 |
| JP | 2003-208207 | 7/2003 |

OTHER PUBLICATIONS

Canadian Patent Office Examiner's Report, issued Jan. 5, 2009 in Canadian Application No. 2,554,055.

* cited by examiner

FIG. 14A

| DIAPER SERIAL No. | SIZE | ... | ABSORBENT CORE SERIAL No. | ADHESION STEP | LEG-HOLE FORMATION STEP | ... | PACKAGE SERIAL No. | PACKAGING STEP |
|---|---|---|---|---|---|---|---|---|
| T00000001 | M | ... | K00000001 | 2004/5/13/13:29 | 2004/5/13/13:30 | ... | P00000001 | 2004/5/14/10:10 |

FIG. 14B

| DIAPER SERIAL No. | ... | PACKAGE INSPECTION STEP | PACKING STEP | PACKING BOX SERIAL No. | PACKING INSPECTION STEP |
|---|---|---|---|---|---|
| T00000001 | ... | 2004/5/20/15:00 | 2004/5/21/10:10 | B00000001 | 2004/5/22/13:10 |

FIG. 14C

| DIAPER SERIAL No. | ··· | STORING STEP | RETRIEVING STEP |
|---|---|---|---|
| T00000001 | ··· | 2004/5/23/11:23 | 2004/5/30/14:50 |

FIG. 14D

| DIAPER SERIAL No. | ··· | SHIPPING STEP | DESTINATION |
|---|---|---|---|
| T00000001 | ··· | 2004/6/07/10:12 | KANAGAWA PREFECTURE |

FIG. 14E

| DIAPER SERIAL No. | ··· | PRODUCT CHECK STEP | DEALER NAME | SELLING STEP |
|---|---|---|---|---|
| T00000001 | ··· | 2004/6/08/13:42 | ... DRUG, ... SHOP | 2004/6/15/10:31 |

FIG. 15A

| PACKAGE SERIAL No. | ... | PACKAGING STEP | PACKAGED CONTENT (DIAPER SERIAL No.) | | | | |
|---|---|---|---|---|---|---|---|
| P00000001 | ... | 2004/5/14/10:10 | T00000001 | T00000002 | T00000003 | T00000004 | T00000005 |

FIG. 15B

| PACKAGE SERIAL No. | ... | PACKAGE INSPECTION STEP | PACKING BOX SERIAL No. | PACKING INSPECTION STEP |
|---|---|---|---|---|
| P00000001 | ... | 2004/5/20/15:00 | B00000001 | 2004/5/22/13:10 |

FIG. 15C

| PACKAGE SERIAL No. | ... | STORING STEP | RETRIEVING STEP |
|---|---|---|---|
| P00000001 | ... | 2004/5/23/11:23 | 2004/5/30/14:50 |

FIG. 15D

| PACKAGE SERIAL No. | ... | SHIPPING STEP | DESTINATION |
|---|---|---|---|
| P00000001 | ... | 2004/6/07/10:12 | KANAGAWA PREFECTURE |

FIG. 15E

| PACKAGE SERIAL No. | ... | PRODUCT CHECK STEP | DEALER NAME | SELLING STEP |
|---|---|---|---|---|
| P00000001 | ... | 2004/6/08/13:42 | ... DRUG. ... SHOP | 2004/6/15/10:31 |

FIG. 16A

| PACKING BOX SERIAL No. | ... | PACKING STEP | PACKED CONTENT (PACKAGE SERIAL No.) | | | PACKED CONTENT (DIAPER SERIAL No.) | | |
|---|---|---|---|---|---|---|---|---|
| B00000001 | ... | 2004/5/21/10:10 | P00000001 | ~ | P00000012 | T00000001 | ~ | T00000060 |

FIG. 16B

| PACKING BOX SERIAL No. | ••• | PACKING INSPECTION STEP |
|---|---|---|
| B00000001 | ••• | 2004/5/22/13:10 |

FIG. 16C

| PACKING BOX SERIAL No. | ••• | STORING STEP | RETRIEVING STEP |
|---|---|---|---|
| B00000001 | ••• | 2004/5/23/11:23 | 2004/5/30/14:50 |

FIG. 16D

| PACKING BOX SERIAL No. | ••• | SHIPPING STEP | DESTINATION |
|---|---|---|---|
| B00000001 | ••• | 2004/6/07/10:12 | KANAGAWA PREFECTURE |

FIG. 16E

| PACKING BOX SERIAL No. | ••• | PRODUCT CHECK STEP | DEALER NAME |
|---|---|---|---|
| B00000001 | ••• | 2004/6/08/13:42 | ... DRUG, ... SHOP |

FIG. 17A

| DIAPER SERIAL No. | SIZE | ... | ABSORBENT CORE SERIAL No. | ADHESION STEP | LEG-HOLE FORMATION STEP | ... | PACKAGE SERIAL No. | PACKAGING STEP |
|---|---|---|---|---|---|---|---|---|
| T00000001 | M | ... | K00000001 | 2004/5/13/13:29 | 2004/5/13/13:30 | ... | P00000001 | 2004/5/14/10:10 |
| T00000002 | M | ... | K00000002 | 2004/5/13/13:29 | 2004/5/13/13:30 | ... | P00000001 | 2004/5/14/10:10 |
| T00000003 | M | ... | K00000003 | 2004/5/13/13:30 | 2004/5/13/13:30 | ... | P00000001 | 2004/5/14/10:10 |
| T00000004 | M | ... | K00000004 | 2004/5/13/13:30 | 2004/5/13/13:31 | ... | P00000001 | 2004/5/14/10:10 |
| T00000005 | M | ... | K00000005 | 2004/5/13/13:31 | 2004/5/13/13:31 | ... | P00000001 | 2004/5/14/10:10 |
| T00000006 | M | ... | K00000006 | 2004/5/13/13:32 | 2004/5/13/13:32 | ... | P00000002 | 2004/5/14/10:12 |
| T00000007 | M | ... | K00000007 | 2004/5/13/13:32 | 2004/5/13/13:32 | ... | P00000002 | 2004/5/14/10:12 |
| T00000008 | M | ... | K00000008 | 2004/5/13/13:32 | 2004/5/13/13:33 | ... | P00000002 | 2004/5/14/10:12 |
| T00000009 | M | ... | K00000009 | 2004/5/13/13:33 | 2004/5/13/13:33 | ... | P00000002 | 2004/5/14/10:12 |
| T00000010 | M | ... | K00000010 | 2004/5/13/13:33 | 2004/5/13/13:34 | ... | P00000002 | 2004/5/14/10:12 |
| ... | ... | ... | ... | ... | ... | ... | ... | ... |

| DIAPER SERIAL No. | ... | PACKAGE INSPECTION STEP | PACKING STEP | PACKING BOX SERIAL No. | PACKING INSPECTION STEP |
|---|---|---|---|---|---|
| T00000001 | ... | 2004/5/20/15:00 | 2004/5/21/10:10 | B00000001 | 2004/5/22/13:10 |
| T00000002 | ... | 2004/5/20/15:00 | 2004/5/21/10:10 | B00000001 | 2004/5/22/13:10 |
| T00000003 | ... | 2004/5/20/15:00 | 2004/5/21/10:10 | B00000001 | 2004/5/22/13:10 |
| T00000004 | ... | 2004/5/20/15:00 | 2004/5/21/10:10 | B00000001 | 2004/5/22/13:10 |
| T00000005 | ... | 2004/5/20/15:00 | 2004/5/21/10:10 | B00000001 | 2004/5/22/13:10 |
| T00000006 | ... | 2004/5/20/15:02 | 2004/5/21/10:10 | B00000001 | 2004/5/22/13:10 |
| T00000007 | ... | 2004/5/20/15:02 | 2004/5/21/10:10 | B00000001 | 2004/5/22/13:10 |
| T00000008 | ... | 2004/5/20/15:02 | 2004/5/21/10:10 | B00000001 | 2004/5/22/13:10 |
| T00000009 | ... | 2004/5/20/15:02 | 2004/5/21/10:10 | B00000001 | 2004/5/22/13:10 |
| T00000010 | ... | 2004/5/20/15:02 | ... | ... | ... |
| ... | ... | | | | |

| DIAPER SERIAL No. | ... | STORING STEP | RETRIEVING STEP |
|---|---|---|---|
| T00000001 | ... | 2004/5/23/11:23 | 2004/5/30/14:50 |
| T00000002 | ... | 2004/5/23/11:23 | 2004/5/30/14:50 |
| T00000003 | ... | 2004/5/23/11:23 | 2004/5/30/14:50 |
| T00000004 | ... | 2004/5/23/11:23 | 2004/5/30/14:50 |
| T00000005 | ... | 2004/5/23/11:23 | 2004/5/30/14:50 |
| T00000006 | ... | 2004/5/23/11:23 | 2004/5/30/14:50 |
| T00000007 | ... | 2004/5/23/11:23 | 2004/5/30/14:50 |
| T00000008 | ... | 2004/5/23/11:23 | 2004/5/30/14:50 |
| T00000009 | ... | 2004/5/23/11:23 | 2004/5/30/14:50 |
| T00000010 | ... | 2004/5/23/11:23 | 2004/5/30/14:50 |
| ⋮ | ... | ⋮ | ⋮ |

| DIAPER SERIAL No. | ... | SHIPPING STEP | DESTINATION |
|---|---|---|---|
| T00000001 | ... | 2004/6/07/10:12 | KANAGAWA PREFECTURE |
| T00000002 | ... | 2004/6/07/10:12 | KANAGAWA PREFECTURE |
| T00000003 | ... | 2004/6/07/10:12 | KANAGAWA PREFECTURE |
| T00000004 | ... | 2004/6/07/10:12 | KANAGAWA PREFECTURE |
| T00000005 | ... | 2004/6/07/10:12 | KANAGAWA PREFECTURE |
| T00000006 | ... | 2004/6/07/10:12 | KANAGAWA PREFECTURE |
| T00000007 | ... | 2004/6/07/10:12 | KANAGAWA PREFECTURE |
| T00000008 | ... | 2004/6/07/10:12 | KANAGAWA PREFECTURE |
| T00000009 | ... | 2004/6/07/10:12 | KANAGAWA PREFECTURE |
| T00000010 | ... | 2004/6/07/10:12 | KANAGAWA PREFECTURE |
| ⋮ | ... | ⋮ | ⋮ |

91

| DIAPER SERIAL No. | ... | PRODUCT CHECK STEP | DEALER NAME | SELLING STEP |
|---|---|---|---|---|
| T00000001 | ... | 2004/6/08/13:42 | ... DRUG, ... SHOP | 2004/6/15/10:31 |
| T00000002 | ... | 2004/6/08/13:42 | ... DRUG, ... SHOP | 2004/6/15/10:31 |
| T00000003 | ... | 2004/6/08/13:42 | ... DRUG, ... SHOP | 2004/6/15/10:31 |
| T00000004 | ... | 2004/6/08/13:42 | ... DRUG, ... SHOP | 2004/6/15/10:31 |
| T00000005 | ... | 2004/6/08/13:42 | ... DRUG, ... SHOP | 2004/6/15/10:31 |
| T00000006 | ... | 2004/6/08/13:42 | ... DRUG, ... SHOP | 2004/6/15/10:31 |
| T00000007 | ... | 2004/6/08/13:42 | ... DRUG, ... SHOP | 2004/6/15/10:31 |
| T00000008 | ... | 2004/6/08/13:42 | ... DRUG, ... SHOP | 2004/6/15/10:31 |
| T00000009 | ... | 2004/6/08/13:42 | ... DRUG, ... SHOP | 2004/6/15/10:31 |
| T00000010 | ... | 2004/6/08/13:42 | ... DRUG, ... SHOP | 2004/6/15/10:31 |

| DIAPER PRODUCT SERIAL No. | PRODUCT MODEL TYPE | STATE OF USAGE |
|---|---|---|
| 00123 | DM001 | USED |
| 00124 | DM001 | UNUSED |
| 00125 | DF002 | UNUSED |
| ⋮ | ⋮ | ⋮ |

| WEARER IDENTIFICATION NUMBER | DIAPER MODEL TYPE | DIAPER LATEST WEARING DATE AND TIME | DIAPER CHANGE INTERVAL | PAD MODEL TYPE | PAD LATEST WEARING DATE AND TIME | PAD CHANGE INTERVAL |
|---|---|---|---|---|---|---|
| P00001 | DM001 | 2005/5/1 / 7:00 | 12 HOURS | PS001 | 2005/5/1 / 6:55 | 2 HOURS |
| P00002 | DM001 | 2005/5/1 / 7:10 | 12 HOURS | PL001 | 2005/5/1 / 7:05 | 3 HOURS |
| P00003 | DF002 | 2005/5/1 / 7:20 | 12 HOURS | PL002 | 2005/5/1 / 7:15 | 3 HOURS |
| ...... | ...... | ...... | ...... | ...... | ...... | ...... |

| WEARER IDENTIFICATION NUMBER | PRODUCT MODEL TYPE | WEARING DATE AND TIME |
|---|---|---|
| P0001 | PS001 | 2005/5/1/ 6:55 |
| P0001 | DM001 | 2005/5/1/ 7:00 |
| P0001 | PS001 | 2005/5/1/ 8:55 |
| P0001 | PS001 | 2005/5/1/10:55 |
| P0001 | PS001 | 2005/5/1/12:55 |
| P0001 | PS001 | 2005/5/1/14:55 |
| P0001 | PS001 | 2005/5/1/16:55 |
| P0001 | PS001 | 2005/5/1/18:55 |
| P0001 | DM001 | 2005/5/1/19:00 |
| P0002 | PL001 | 2005/5/1/ 7:05 |
| P0002 | DM001 | 2005/5/1/ 7:10 |
| P0002 | PL001 | 2005/5/1/10:05 |
| P0002 | PL001 | 2005/5/1/13:05 |
| ⋮ | ⋮ | ⋮ |

| PRODUCT MODEL TYPE | PRICE |
|---|---|
| DM001 | 120 YEN |
| DM002 | 150 YEN |
| DF001 | 120 YEN |
| DF002 | 150 YEN |
| PS001 | 12 YEN |
| PS002 | 15 YEN |
| PL001 | 20 YEN |
| PL002 | 30 YEN |
| ⋮ | ⋮ |

| WEARER IDENTIFICATION NUMBER | SELF-PAY RATIO | BILLING AMOUNT |
|---|---|---|
| P0001 | 10% | 32 YEN |
| P0002 | 10% | 34 YEN |
| P0003 | 100% | 510 YEN |
| ⋮ | ⋮ | ⋮ |

| FACILITY IDENTIFICATION NUMBER | PRODUCT MODEL TYPE | STOCK NUMBER |
|---|---|---|
| H 0 0 1 | D M 0 0 1 | 1 0 0 |
| H 0 0 1 | D M 0 0 2 | 1 5 0 |
| ⋮ | ⋮ | ⋮ |
| H 0 0 1 | P S 0 0 1 | 3 0 0 |
| H 0 0 1 | P S 0 0 2 | 5 0 0 |
| ⋮ | ⋮ | ⋮ |
| H 0 0 2 | D M 0 0 1 | 5 0 |
| H 0 0 2 | D F 0 0 1 | 3 0 |
| ⋮ | ⋮ | ⋮ |

# DIAPER PRODUCT, SUPPLY INFORMATION MANAGEMENT SYSTEM, USAGE INFORMATION MANAGEMENT SYSTEM AND DIAPER PRODUCT MANAGEMENT SYSTEM

TECHNICAL FIELD

The present invention relates to a diaper product and a supply information management system, a usage information management system and a diaper product management system for managing information on the diaper products.

BACKGROUND ART

In the field of diaper products such as disposal diapers (i.e. disposable diapers), conventionally, various kinds of products have been used, depending on sex or health and body conditions of wearers, purpose of use or the like. Therefore, in facilities where a large number of diaper products are used, such as hospitals or nursing homes for the aged, much labor and effort is required in operations for stock control of the diaper products or the like.

Japanese Patent Application Laid Open Gazette Nos. 2002-150057 and 2003-58759 propose a technique for stock control and sales management in which a bar code is attached to a disposal diaper and the information (serial number and the like) on the disposal diaper is read out from the bar code.

In general, however, a disposal diaper is provided with elastic members over a wide range so as to be fitted well to the skin of a wearer, and with the elasticity of the elastic members, the disposal diaper has a contracted form as a whole. For this reason, in the case shown in Japanese Patent Application Laid Open Gazette Nos. 2002-150057 and 2003-58759 where a bar code is attached to a disposal diaper, there is a possibility that contraction of the disposal diaper may distort the notation of bar code or hide part of the bar code and the information can not be read out from the bar code.

There are some requests also for stock control or the like of auxiliary absorbent pads such as absorbent pads to be attached inside the disposal diapers, but since the auxiliary absorbent pad is also provided with elastic members over a wide range, there are some cases where the information can not be read out from the attached bar code.

On the other hand, since the disposal diaper is distributed through processes of manufacture, inspection, storage, shipment, sale and the like, being packaged by a package bag or the like, the bar code which is attached to the disposal diaper packaged by a package bag can not be read out. Though it is possible to attach a bar code to a package bag or a packing box, if many kinds of package bags or the like are used, it is necessary to place the package bags in the same direction so that the bar codes thereon should face this side in order to find a specified package bag or the like, and therefore it is hard to increase working efficiency of the above processes.

Further, there is a request for a management system which allows a proper and easy check on information on operation being performed in each of the above processes or the like, for individual disposal diapers, auxiliary absorbent pads or the like.

DISCLOSURE OF INVENTION

The present invention is intended for a diaper product and systems for managing supply and usage of the diaper products, and it is an object of the present invention to specify individual diaper products and perform a proper and easy management of information on supply and usage of the diaper products.

According to the present invention, the diaper product comprises an absorbent product for receiving excrement from a wearer and an IC tag having an IC chip and an antenna for radio communication connected to the IC chip, which is attached to the absorbent product, and in the diaper product, a serial number for discriminating the absorbent product from other absorbent products is stored in the IC chip and can be read out through the antenna. This makes it possible to reliably read a serial number of a diaper product.

Preferably, the diaper product includes a disposal diaper, and further includes a product which is used with an auxiliary absorbent pad and a product where a plurality of absorbent products are packaged by a package. In a case where the disposal diaper and the auxiliary absorbent pad are used together, it is preferable that IC tags should be individually attached to the disposal diaper and the auxiliary absorbent pad.

According to the present invention, a supply information management system for managing information on supply of diaper products comprises a writing device provided in a station where for a diaper product provided with an IC tag where information can be written to and read from an IC chip through an antenna for radio communication, a predetermined process for at least one of manufacture, inspection, storage, shipment and sale on supply of the diaper product is performed, which writes and stores process information on the predetermined process to the IC chip of the diaper product, a reading device for reading the process information together with a serial number stored in the IC chip in advance, a product database storage part for storing a product database which is a set of data elements each associating the serial number with the process information, and a product database updating part for specifying a data element in the product database, which includes the serial number read out by the reading device, and adding the process information read out by the reading device to the data element.

The supply information management system of the present invention allows a proper and easy management of information on supply of diaper products and secures traceability of the diaper products. The IC tag where information can be only read out from the IC chip may be used, and in this case, the product database is stored in a predetermined storage part and updated with reference to a serial number which is read out from the IC chip.

According to the present invention, a usage information management system for managing information on usage of diaper products comprises a reading device for reading a product model type indicating the kind of diaper product and a serial number which are stored in advance in an IC chip of the diaper product provided with an IC tag where information can be read out from the IC chip through an antenna for radio communication, a stock database storage part for storing a stock database which is a set of data elements each associating the serial number of the diaper product with the product model type and the state of usage of the diaper product, a stock database updating part operating when one diaper product is put on a wearer of the diaper product, for specifying a data element in the stock database which includes a serial number of the diaper product, which is read out by the reading device, and updating the value of a data item in the data element which indicates the state of usage from a value of "unused" to that of "used", and a stock number obtaining part operating on each of a plurality of product model types for the diaper product, for specifying data elements in the stock database, each of which includes one product model type and a data item indicating the state of usage which has the value of "unused", and obtaining the number of data elements as a stock number for a diaper product corresponding to the product model type. The usage information management system reduces a burden in stock control operation.

According to the present invention, another usage information management system for managing information on usage of diaper products comprises a first reading device for reading a product model type indicating the kind of diaper product, which is stored in advance in an IC chip of the diaper product provided with an IC tag where information can be read out from the IC chip through an antenna for radio communication, a second reading device for reading a wearer identification number for discriminating one wearer of a diaper product from other wearers in a predetermined manner, a wearer database storage part for storing a wearer database which is a set of data elements each associating the wearer identification number with an applicable model type which is a product model type of a diaper product to be put on a wearer corresponding to the wearer identification number, and a model type check part operating when one diaper product is put on a wearer, for specifying a data element in the wearer database, which includes a wearer identification number read out by the second reading device, and checking an applicable model type in the data element with the product model type of the diaper product read out by the first reading device. This usage information management system reduces a burden in changing the diaper product.

Preferably, the data element of the wearer database includes latest wearing date and time associated with the wearer identification number, and this allows a reliable management of change-scheduled date and time. Still preferably, a usage frequency of the diaper product is obtained in this system.

The present invention is also intended for a diaper product management system comprising a supply information management system and a usage information management system for the diaper products, and this makes it possible to perform a comprehensive management of the diaper products by associating information on supply and usage of the diaper products with one another.

These and other objects, features, aspects and advantages of the present invention will become more apparent from the following detailed description of the present invention when taken in conjunction with the accompanying drawings.

BRIEF DESCRIPTION OF DRAWINGS

FIG. 14A is a view showing information stored in an IC tag of the tagged diaper in the manufacturing station;

FIG. 14B is a view showing information stored in the IC tag of the tagged diaper in the inspection station;

FIG. 14C is a view showing information stored in the IC tag of the tagged diaper in the storage station;

FIG. 14D is a view showing information stored in the IC tag of the tagged diaper in the shipping station;

FIG. 14E is a view showing information stored in the IC tag of the tagged diaper in the sales station;

FIG. 15A is a view showing information stored in an IC tag of the tagged package in the manufacturing station;

FIG. 15B is a view showing information stored in the IC tag of the tagged package in the inspection station;

FIG. 15C is a view showing information stored in the IC tag of the tagged package in the storage station;

FIG. 15D is a view showing information stored in the IC tag of the tagged package in the shipping station;

FIG. 15E is a view showing information stored in the IC tag of the tagged package in the sales station;

FIG. 16A is a view showing information stored in an IC tag of the tagged packing box in the manufacturing station;

FIG. 16B is a view showing information stored in the IC tag of the tagged packing box in the inspection station;

FIG. 16C is a view showing information stored in the IC tag of the tagged packing box in the storage station;

FIG. 16D is a view showing information stored in the IC tag of the tagged packing box in the shipping station;

FIG. 16E is a view showing information stored in the IC tag of the tagged packing box in the sales station;

FIG. 17A is a view showing a product database;

FIG. 17B is a view showing a product database;

FIG. 17C is a view showing a product database;

FIG. 17D is a view showing a product database;

FIG. 23 is a view showing a stock database;

FIG. 24 is a view showing a wearer database;

FIG. 25 is a view showing a wearing date and time database;

FIG. 26 is a view showing a price database;

FIG. 27 is a view showing a billing database;

FIG. 29 is a view showing a consumer stock database.

DETAILED DESCRIPTION OF THE INVENTION

Figure 1:
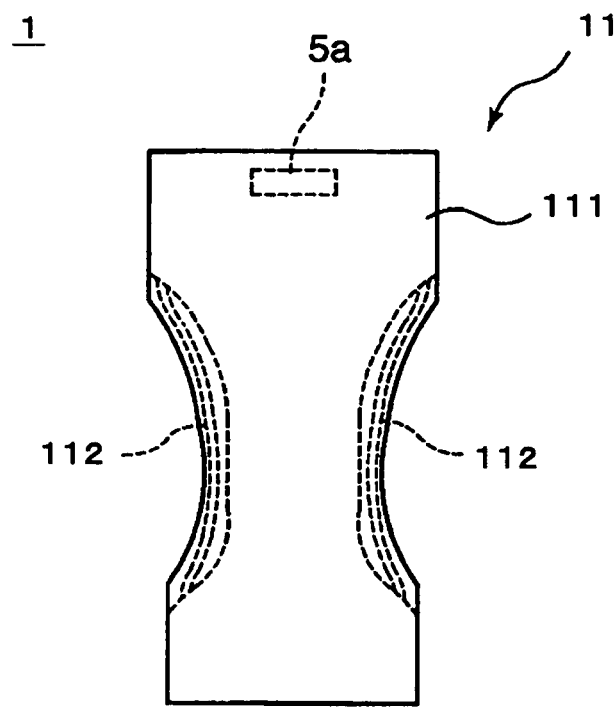
FIG. 1 is a plan view showing a tagged core in accordance with a preferred embodiment of the present invention.

FIG. 1 is a view showing an IC-tagged absorbent core (hereinafter, referred to as "tagged core") 1 which is a diaper product. As shown in FIG. 1, the tagged core 1 comprises an absorbent core 11 which is an absorbent product for receiving an excrement from a wearer thereof and an IC tag 5a attached to the absorbent core 1.

The absorbent core 11 comprises a body sheet 111 having a form of hourglass and an absorbent (not shown) adhered on the body sheet 111, and is used together with an outer covering sheet 211 of a disposal diaper 21 (see FIG. 2) which is discussed later. The body sheet 111 is formed by adhering a pair of sheets layered in a direction of thickness one on another. Between these sheets, elastic members 112 are provided, being extended, and the IC tag 5a is adhered. The IC tag 5a may be adhered outside the absorbent core 11 (opposite to the wearer side).

The IC tag 5a comprises an IC chip which is capable of storing various information, an antenna for radio communication which is connected to the IC chip and a control part for performing the encoding and decoding process of the information which are sent or received through the antenna, though detailed description is omitted here as it is well known. In the IC chip of the IC tag 5a, a serial number for discriminating the absorbent core 11 from other absorbent cores is stored in advance and can be read out through the antenna for radio communication. The antenna may be formed directly on the IC chip (the same applies to other IC chips in the following discussion).

Figure 2:
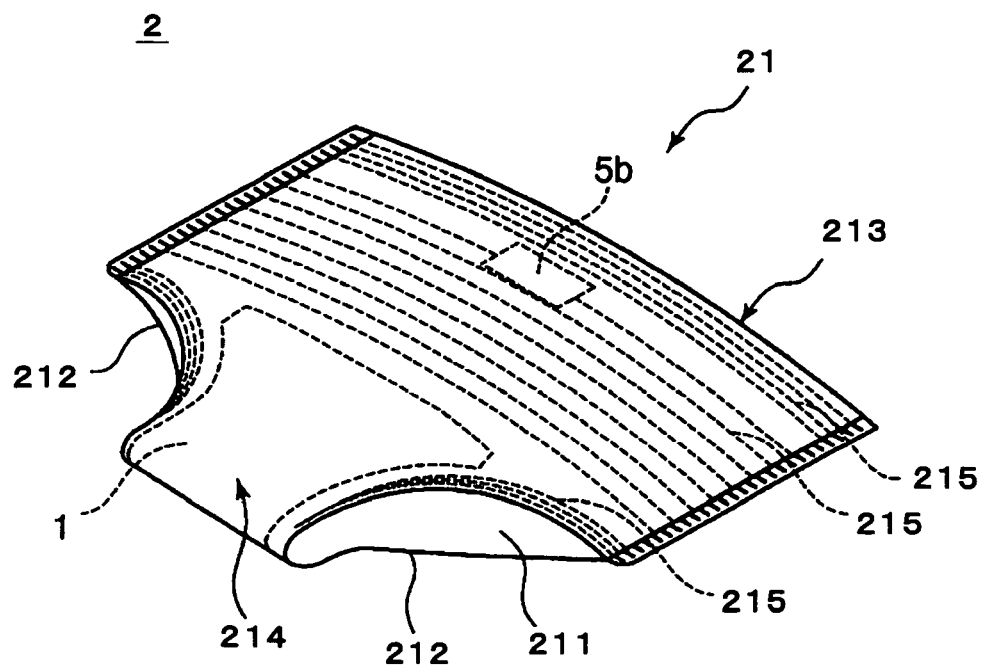
FIG. 2 is a perspective view showing a tagged diaper in accordance with the preferred embodiment of the present invention.

FIG. 2 is a view showing an IC-tagged disposal diaper (hereinafter, referred to as "tagged diaper") 2 which is another type of diaper product. As shown in FIG. 2, the tagged diaper 2 comprises a disposal diaper 21 which is an absorbent product for receiving an excrement from a wearer thereof and an IC tag 5b attached to the disposal diaper 21.

The disposal diaper 21 comprises the outer covering sheet 211 and the tagged core 1, and the folio outer covering sheet 211 is adhered along its side ends from upper ends of notches 212 which are openings for legs to a waist opening 213 to form a shape of underpants. The tagged core 1 is adhered inside part of the outer covering sheet 211 which corresponds to a crotch part 214 (on the side of wearer) to absorb an excrement of a wearer.

The outer covering sheet 211 is formed of a pair of sheets which are layered in the direction of thickness and adhered one on another, and between these sheets, elastic members 215 are provided, being extended, and the IC tag 5b is adhered. The IC tag 5b has the same constitution as the IC tag 5a (see FIG. 1) and in the IC chip of the IC tag 5b, a serial number and the like (see FIGS. 14A to 14E) for discriminating the disposal diaper 21 from other disposal diapers are stored and can be read out through the antenna for radio communication.

The IC tag 5b may be adhered outside the disposal diaper 21 (opposite to the wearer side of the outer covering sheet 211 formed of a pair of sheets layered one on another). An outer sheet of the outer covering sheet 211 is usually waterproof and the IC tag 5b is thereby prevented from being in contact with moisture from the wearer. This allows the IC tag 5b to be attached to the disposal diaper 21 without waterproofing (e.g., coating with resin) even if the IC tag 5b is such a type as deteriorates its performance by contact with moisture or the like.

Figure 3:
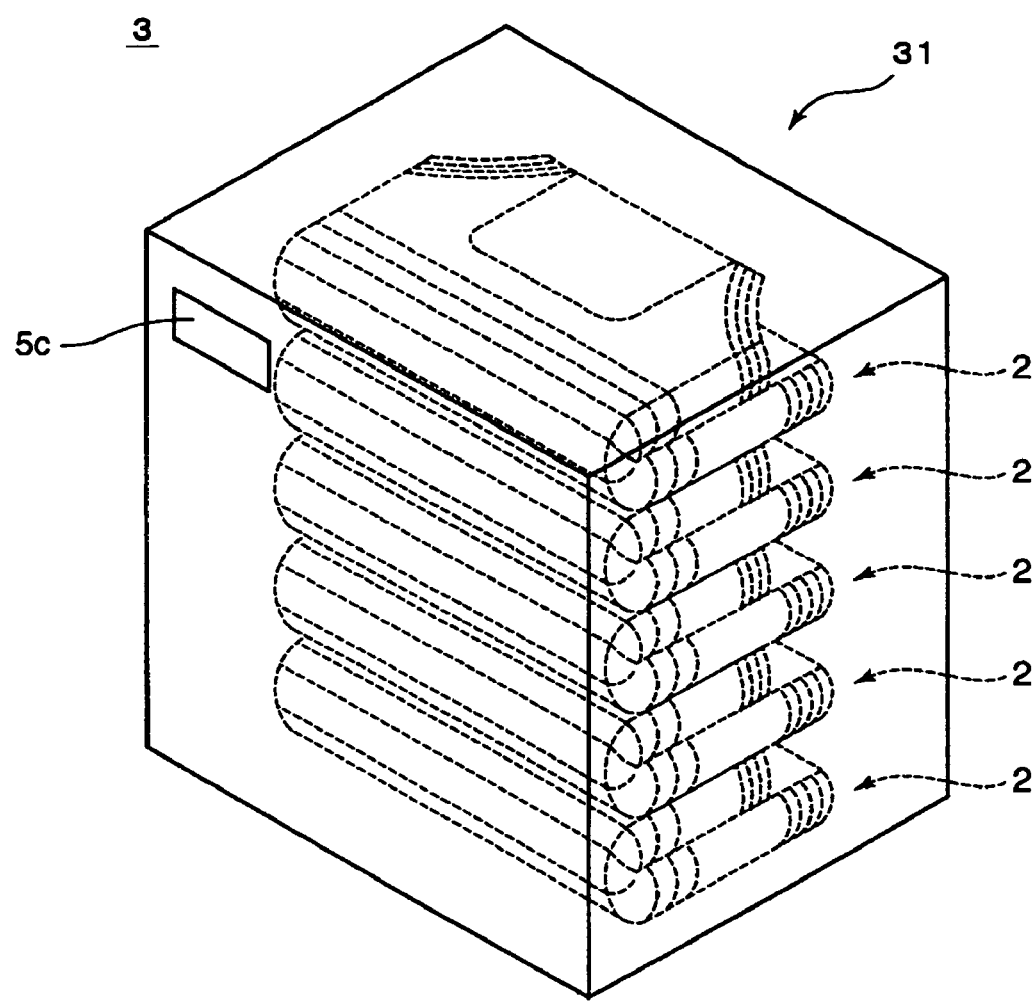
FIG. 3 is a perspective view showing a tagged package in accordance with the preferred embodiment of the present invention.

FIG. 3 is a view showing an IC-tagged diaper package (hereinafter, referred to as "tagged package") 3 which is still another type of diaper product. As shown in FIG. 3, the tagged package 3 comprises a plurality of tagged diapers 2 (five tagged diapers in FIG. 3), a diaper package 31 which is a package for packaging a plurality of tagged diapers 2 and an IC tag 5c attached to the diaper package 31.

As shown in FIG. 3, the diaper package 31 is a substantially rectangular box which contains a plurality of folded tagged diapers 2 and the IC tag 5c is affixed to the upper left on its front. Like the IC tag 5a (see FIG. 1), the IC tag 5c comprises an IC chip which is capable of storing various information, an antenna for radio communication which is connected to the IC chip and a control part for performing the encoding and decoding process of the information which are sent or received through the antenna. In the IC chip of the IC tag 5c, a serial number and the like (see FIGS. 15A to 15E) for discriminating the diaper package 31 from other diaper packages are stored and can be read out through the antenna.

Figure 4:
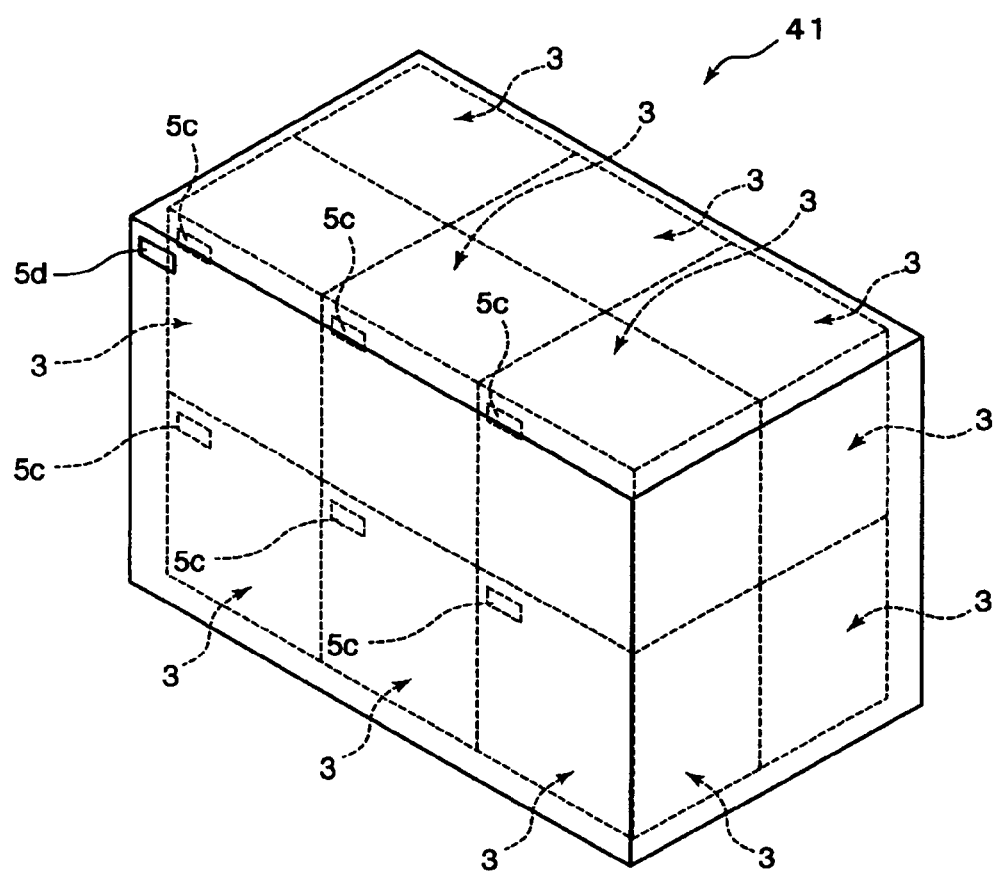
FIG. 4 is a perspective view showing a tagged packing box in accordance with the preferred embodiment of the present invention.

FIG. 4 is a view showing an IC-tagged diaper packing box (hereinafter, referred to as "tagged packing box") 4. As shown in FIG. 4, the tagged packing box 4 comprises a plurality of tagged packages 3 (twelve tagged packages in FIG. 4), a packing box 41 in which a plurality of tagged packages 3 are packed and an IC tag 5d attached to the packing box 41. The packing box 41 can be considered as an indirect package for a plurality of tagged diapers 2.

As shown FIG. 4, the packing box 41 is a substantially rectangular box which contains a plurality of tagged packages 3 and the IC tag 5d is affixed to the upper left on its front. The IC tag 5d has the same constitution as the IC tag 5a (see FIG. 1) and in the IC chip of the IC tag 5d, a serial number and the like (see FIGS. 16A to 16E) for discriminating the packing box 41 from other packing boxes are stored and can be read out through the antenna for radio communication.

Next, discussion will be made on a supply information management system 710 for managing information on supply of the above diaper products (i.e., the tagged core 1, the tagged diaper 2, the tagged package 3 and the tagged packing box 4). In the following discussion, the IC tags 5a to 5d attached to the diaper products are generally termed as an IC tag 5 if these IC tags are not distinguished from each other. In the IC tag 5, information is written to the IC chip through the antenna for radio communication and read out from the IC chip.

Figure 5:
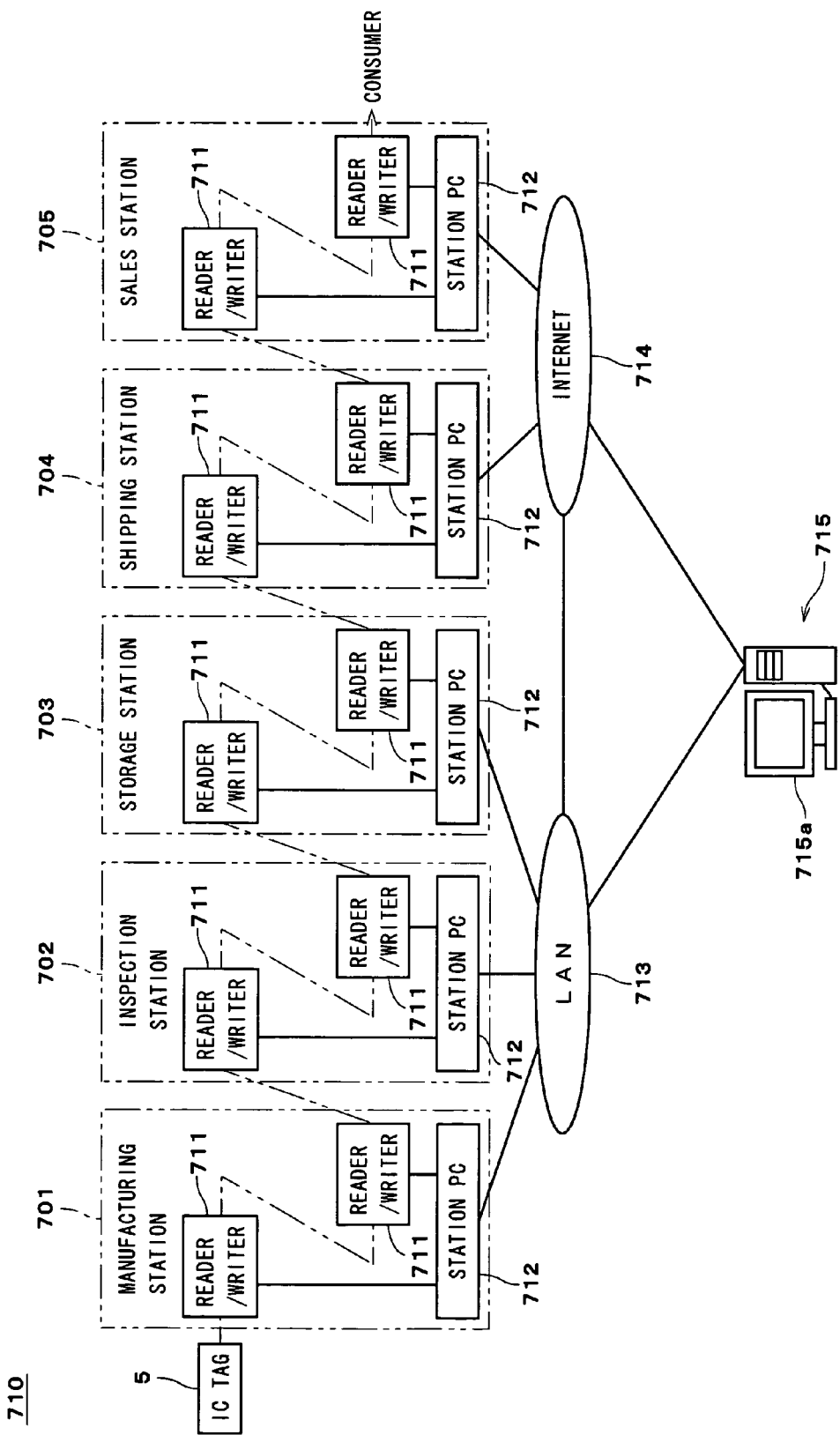
FIG. 5 is a view showing a supply information management system in accordance with the preferred embodiment of the present invention.

FIG. 5 is a view showing the supply information management system 710. As shown in FIG. 5, a diaper product is distributed to a customer mainly through a manufacturing station 701, an inspection station 702, a storage station 703, a shipping station 704 and a sales station 705 (hereinafter, referred to simply as "stations 701 to 705" if these five stations are collectively mentioned to) where respective processes on supply of the diaper product, i.e., manufacture, inspection, storage (i.e., storing and retrieving), shipment and sale, are performed. In the supply information management system 710, an execution order of these processes executed for the diaper product is set in the order of reference numbers of stations 701 to 705.

The supply information management system 710 comprises a reader/writer 711 which is provided in each of the stations 701 to 705 and capable of having communication with the IC tag 5 in a noncontact manner, a station personal computer (hereinafter, referred to as "station PC") 712 provided in each station, having communication with the reader/ writer 711, and a host computer 715 which is a management device for having communication with the station PC 712 through LAN 713 or internet 714. In the supply information management system 710, the host computer 715 makes a product database 91 (see FIGS. 17A to 17E) by associating information in the IC tag 5 which is read out by the reader/writer 711 with each serial number and storing the information. The product database 91 is displayed on a display 715a.

With an instruction of the station PC 712, each reader/writer 711 writes and stores process information on the process executed in one of the stations 701 to 705 where the reader/writer 711 is set into the IC chip of the IC tag 5 of the diaper product, and on the other hand, the reader/writer 711 reads the process information which has been written to the IC chip and the serial number stored in the IC chip in advance, out from the IC tag 5 of the diaper product passing through the stations 701 to 705. In other words, the reader/writer 711 is a writing device for writing the process information on the diaper product to the IC chip of the IC tag 5 of the diaper product and a reading device for reading the process information out from the IC chip of the diaper product.

Specifically, the reader/writer 711 comprises an antenna for sending and receiving information through the antenna of the IC tag 5 and supplying electric power for the IC tag 5, a control part for performing the encoding and decoding process of the information which is sent or received through this antenna and a communication part for having communication with the station PC 712, and is capable of having communication with the IC tag 5 in a noncontact manner.

Figure 7:
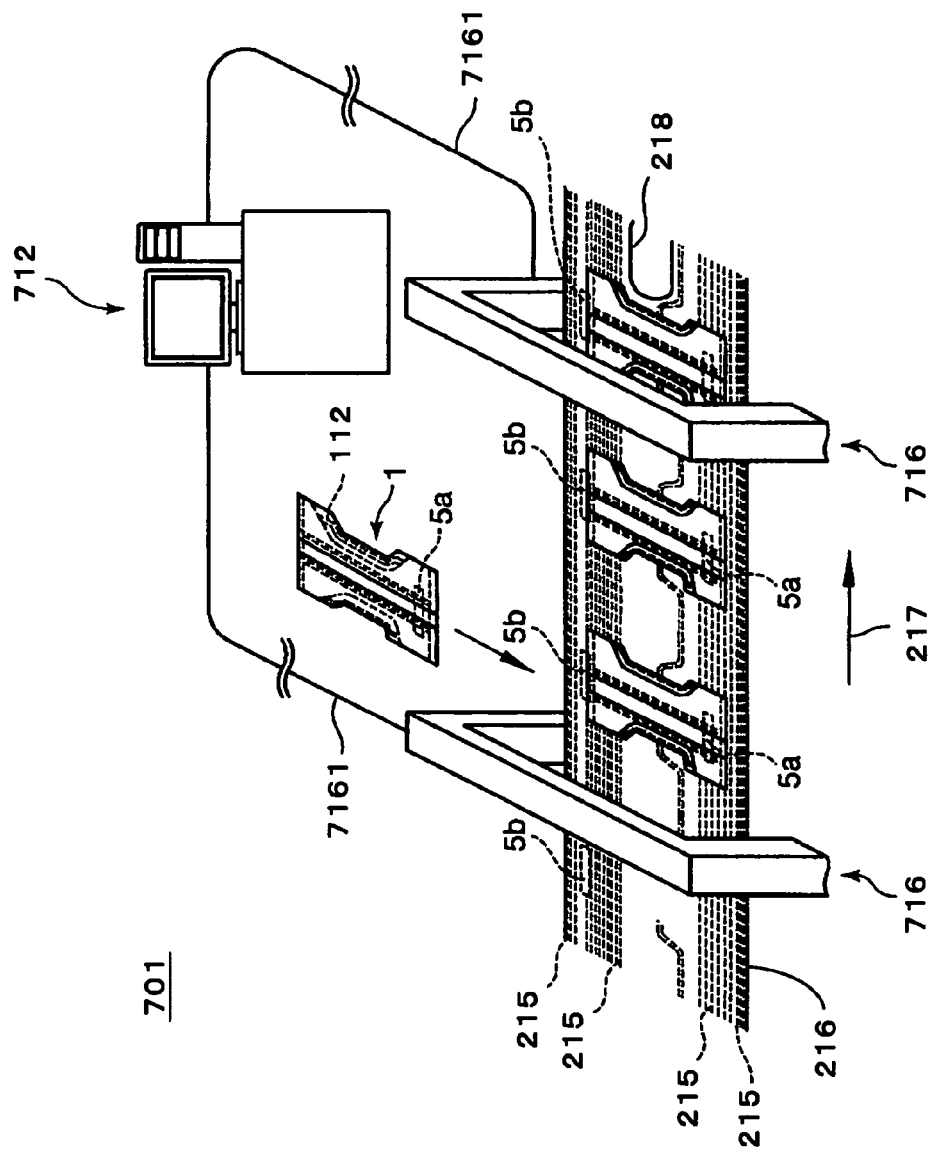
FIG. 7 is a perspective view showing part of a manufacturing station.
Figure 11:
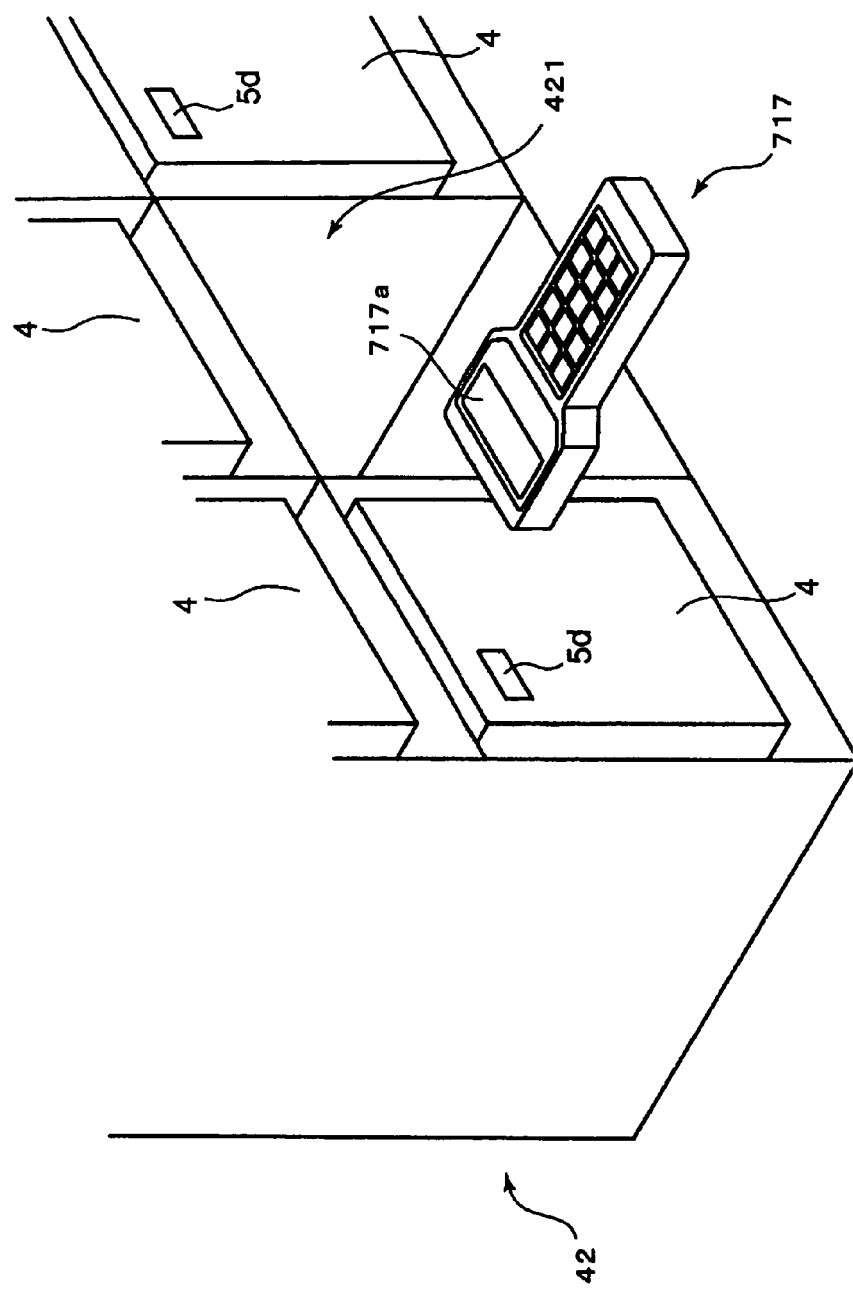
FIG. 11 is a perspective view showing an enlarged part of a handy type reader/writer and a storage shelf.

Among various types of reader/writers 711 are, for example, a gate type reader/writer 716 shown in FIG. 7 and a handy type reader/writer 717 which is portable (i.e., a portable reading device) shown in FIG. 11. The gate type reader/writer 716 (see FIG. 7) is connected to the station PC 712 through a cable 7161 or the like to have communication therewith, and the handy type reader/writer 717 (see FIG. 11) is connected to the station PC 712 through a cradle (not shown) or the like to have communication therewith, however, the communication manner is not particularly limited to these but, for example, there may be a case where the gate type reader/writer 716 and handy type reader/writer 717 have radio communication with the station PC 712.

As shown in FIG. 11, the handy type reader/writer 717 comprises a display panel 717a consisting of an LCD (liquid crystal display) and the like. In the handy type reader/writer 717, since the serial number and the process information read out from the IC tag 5 are outputted on the display panel 717a, an operator can check the serial number and the like on site.

Figure 6:
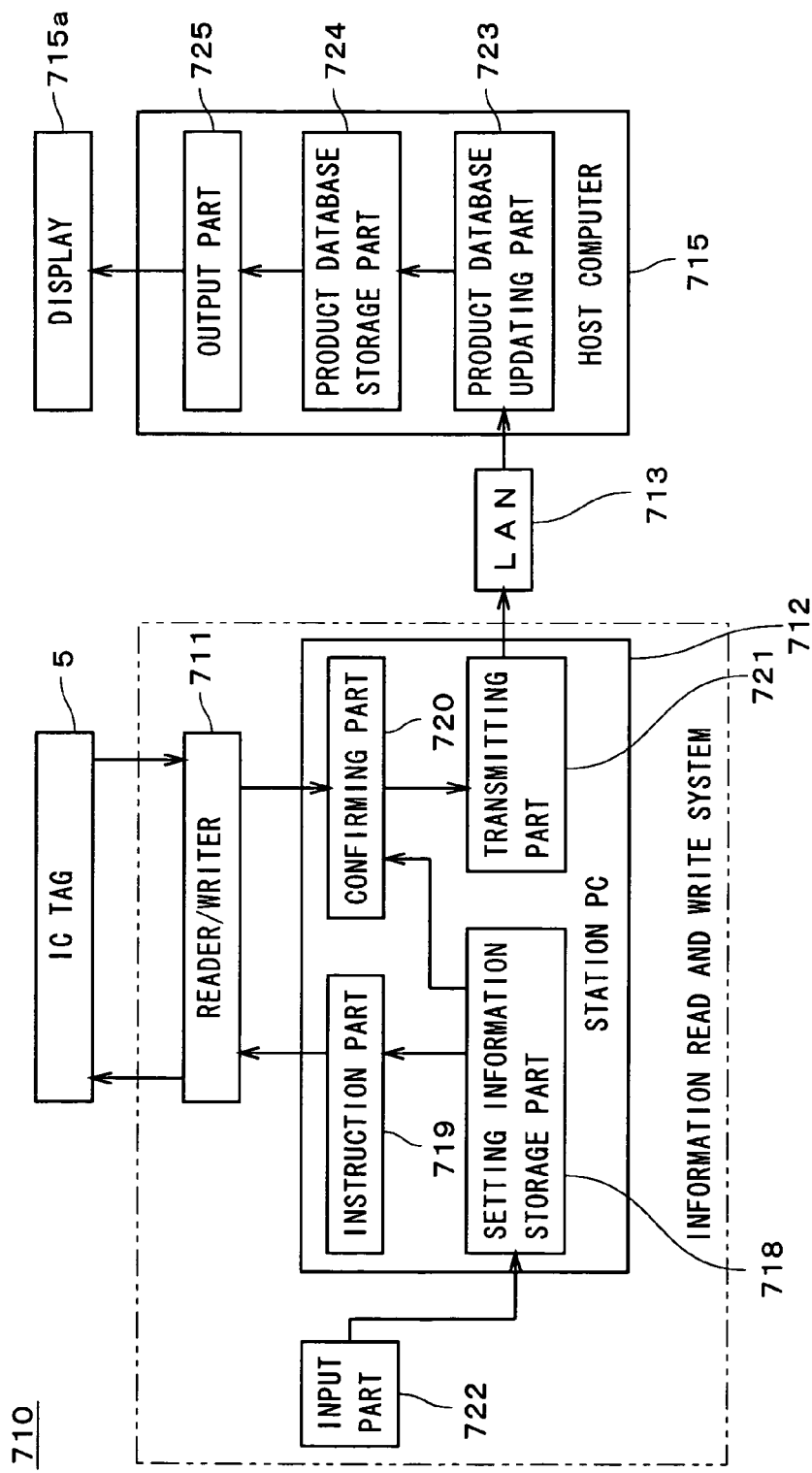
FIG. 6 is a block diagram showing functions of the supply information management system.

FIG. 6 is a block diagram showing a functional constitution of the supply information management system 710. The station PC 712 has constituent elements like those in an ordinary computer, such as a CPU for performing various computations, a ROM for storing an initial setting and the like and a RAM used as a storage area for various information, and mainly functions as a setting information storage part 718, an instruction part 719, a confirming part 720 and a transmitting part 721, as shown in FIG. 6.

The setting information storage part 718 stores the contents of the process information (hereinafter, referred to as "written information") to be stored into the IC tag 5 through the reader/writer 711 connected to the station PC 712 and the process information (hereinafter, referred to as "recorded information") that should have been already stored in the IC tag 5 when it is read by the reader/writer 711. Specifically, the setting information storage part 718 stores the contents of the above information (i.e., written information and recorded information) in accordance with an input from an input part 722 such as a keyboard or a mouse connected to the station PC 712.

The instruction part 719 gives such an instruction as to store the written information stored in the setting information storage part 718 into the IC tag 5, to the reader/writer 711 connected to the station PC 712.

The confirming part 720 confirms whether the information received from the reader/writer 711 (i.e., the process information which has been read out by the reader/writer 711) between one of the processes to be executed in the stations 701 to 705 (hereinafter, referred to as "first process") and a process to be executed subsequently to the first process (hereinafter, referred to as "second process") includes the written information (hereinafter, referred to as "first process information") to be written to the IC tag 5 by the reader/writer 711, by comparing with the recorded information stored in the setting information storage part 718.

If it is confirmed that the first process information is included in the process information read out by the reader/writer 711 (e.g., the gate type reader/writer 716 or the handy type reader/writer 717), the first process information and the serial number read out by the reader/writer 711 are transmitted to the host computer 715 by the transmitting part 721 through the LAN 713. Though only the LAN 713 is shown in FIG. 6, the serial number can be transmitted through the internet 714 instead of the LAN 713. On the other hand, if it is confirmed by the confirming part 720 that the first process information is not included in the information read out by the reader/writer 711, a report that the processes for the diaper product are not executed in the normal order is given to the operator or the like in various notifying manners (e.g., lighting of a warning light).

In the supply information management system 710, the reader/writer 711, the station PC 712 and the input part 722 constitute one example of information read and write system for reading and writing the information to the diaper product.

On the other hand, the host computer 715 has a constitution of the CPU, the ROM, the RAM and the like, like the station PC 712, and mainly functions as a product database updating part 723, a product database storage part 724 and an output part 725.

The product database storage part 724 stores the product database 91 (see FIGS. 17A to 17E) which is a set of data elements each associating the serial number of the diaper product with the process information on the processes of manufacture and the like which are executed for the diaper product in the stations 701 to 705. As shown in FIGS. 17A to 17E, in the product database 91, a plurality of data elements corresponding to a plurality of tagged diapers 2 are listed in the vertical direction and the information on the operations performed in the processes of manufacture and the like for the tagged diapers 2 are listed in the horizontal direction.

The product database updating part 723 receives the information (i.e., the serial number and the process information) transmitted from the transmitting part 721 of the station PC 712 to specify the data element including the serial number in the product database 91 on the basis of the serial number received from the station PC 712, and adds the received process information to the specified data element. When the information corresponding to a new serial number is inputted, the product database updating part 723 additionally registers a data element corresponding to this new serial number in the product database 91.

The output part 725 displays the product database 91 stored in the product database storage part 724 on the display 715a.

Next, the operation performed by the supply information management system 710 in each of the stations 701 to 705 will be discussed, taking an example.

FIG. 7 is a perspective view showing part of the manufacturing station 701. FIG. 7 shows an adhesion step which is one exemplary step of the manufacturing process executed in the manufacturing station 701, and in this adhesion step, an outer covering sheet forming band 216 used for forming the outer covering sheet 211 is transferred along a direction of line indicated by the arrow 217 and the tagged core 1 is adhered onto the outer covering sheet forming band 216.

In the manufacturing station 701, the gate type reader/writers 716 are provided on the upstream and downstream sides of a position where the adhesion step is executed, and these gate type reader/writers 716 can have communication with the station PC 712 through the cable 7161.

The outer covering sheet forming band 216 is so transferred as to pass the gate type reader/writers 716, and the elastic members 215 and the IC tag 5b are already attached to the outer covering sheet forming band 216 before the outer covering sheet forming band 216 passes the upstream-side gate type reader/writer 716. In the IC tag 5b, as shown in FIG. 14A, the serial number of the tagged diaper 2 (diaper serial No. in FIG. 14A), the size, the process information on steps previous to the adhesion step (e.g., dates and times when the previous steps are executed) are stored.

When the IC tag 5b passes the upstream-side gate type reader/writer 716, first, the gate type reader/writer 716 reads the information stored in the IC tag 5b and the confirming part 720 confirms whether this information includes the process information on the previous step (e.g., the date and time when a step of attaching the elastic members 215 is executed). If it is confirmed that the process information on the previous step is not included in this information, the station PC 712 gives a report of abnormality to the operator. If it is confirmed that the process information on the previous step is included in this information, the step of adhering the tagged core 1 is executed.

When the adhesion step is finished and the IC tag 5b passes the downstream-side gate type reader/writer 716, this gate type reader/writer 716 reads the serial number of the tagged core 1 which is stored in the IC tag 5a of the tagged core 1 and the serial number (absorbent core serial No. in FIG. 14A) and the execution date and time of the adhesion step (i.e., the date and time when the IC tag 5b passes the downstream-side gate type reader/writer 716) are written to the corresponding IC tag 5b of the outer covering sheet forming band 216 (i.e., the IC tag 5b corresponding to a position where the tagged core 1 is adhered onto the outer covering sheet forming band 216).

At the same time, the serial number stored in the IC tag 5b in advance (i.e., the serial number of the tagged diaper 2) is read out by the gate type reader/writer 716 and transmitted to the host computer 715 of FIG. 6 together with the serial number of the tagged core 1 and the execution date and time of the adhesion step. Then, the product database updating part 723 adds the serial number of the tagged core 1 and the execution date and time of the adhesion step to the data element in the product database 91 (see FIGS. 17A to 17E) corresponding to the IC tag 5b.

After that, as to the subsequent manufacturing step, e.g., a leg-hole formation step of forming the notches 218 for leg-holes, the gate type reader/writer 716 provided on the further downstream side writes the execution date and time of the step and the like to the IC tag 5b (see FIG. 14A).

When more steps in the manufacturing process are executed to finally complete the tagged diaper 2, a packaging step of manufacturing the tagged package 3 in which a plurality of tagged diapers 2 are put in the diaper package 31 is executed in the manufacturing station.

Though not shown, in the packaging step of the tagged diapers 2, the diaper package 31 provided with the IC tag 5c (see FIG. 3) is transferred along the direction of line and five tagged diapers 2 are sequentially put into the diaper package 31 to manufacture the tagged package 3. Like the above adhesion step, the gate type reader/writers 716 are provided on the upstream and downstream sides of a position where the packaging step is executed and the diaper package 31 (or the manufactured tagged package 3) is so transferred as to pass these gate type reader/writers 716. When the diaper package 31 passes the upstream-side gate type reader/writer 716, like in the adhesion step, confirmation is made on whether there is process information on the previous step or not.

On the other hand, when the tagged package 3 passes the downstream-side gate type reader/writer 716, the serial number is read out by the gate type reader/writer 716 from the IC tag 5c attached to the diaper package 31 and as shown in FIG. 14A, the serial number (package serial No. in FIG. 14A) and the execution date and time of the packaging step (i.e., the date and time where the tagged package 3 passes the downstream-side gate type reader/writer 716) are written to the IC tag 5b on each of the five tagged diapers 2 contained in the diaper package 31.

Concurrently with this, the serial number of the tagged diaper 2 is read out from the IC tag 5b on each of a plurality of contained tagged diapers 2 by the downstream-side gate type reader/writer 716 and as shown in FIG. 15A, the serial number together with the execution date and time of the packaging step is written to the IC tag 5c of the tagged package 3.

As the information to be stored in the IC tags 5a to 5c in the manufacturing station 701, besides the above items, there are, for example, brand information of the disposal diaper 21 (see FIG. 2) (e.g., product names), types for men or women, and the like. Further, in the IC tags 5a to 5c, product model types indicating the kind of the disposal diaper 21 (i.e., identification codes of product including the brand information such as product names, or other information such as size and types for men or women) may be stored.

Figure 8:
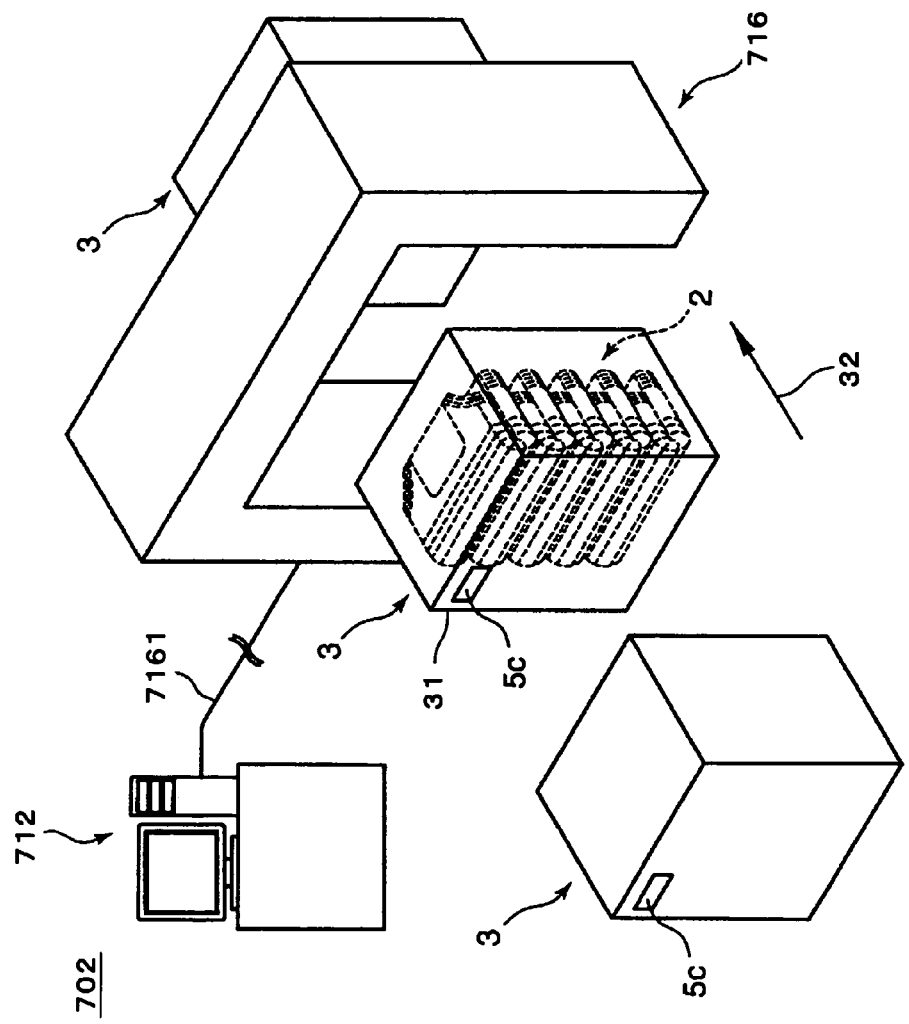
FIG. 8 is a perspective view showing part of an inspection station.

FIG. 8 is a perspective view showing part of the inspection station 702. FIG. 8 shows a package inspection step which is one exemplary step of the process executed in the inspection station 702. In the package inspection step, as shown in FIG. 8, the tagged package 3 is transferred along a direction of line indicated by the arrow 32 and an inspection is made on whether the diaper package 31 contains a predetermined number of tagged diapers 2 (five in FIG. 8) or not.

In the inspection station 702, the gate type reader/writers 716 are provided on the upstream and downstream sides of a position where the package inspection step is executed (the upstream-side one is not shown), and the gate type reader/writers 716 can have communication with the station PC 712 through the cable 7161. The tagged package 3 is so transferred as to pass these gate type reader/writers 716.

When the tagged package 3 passes the upstream-side gate type reader/writer 716, like in the above steps, the gate type reader/writer 716 reads the information stored in the IC tag 5b of the tagged diaper 2 and a confirmation is made on whether this information includes the process information on the previous step or not. If it is confirmed that the process information on the previous step is not included in this information, the station PC 712 gives a report of abnormality to the operator. On the other hand, if it is confirmed that the process information on the previous step is included in this information, the package inspection step is executed.

In the package inspection step, when the tagged package 3 passes the downstream-side gate type reader/writer 716, the serial number of the tagged diaper 2 is read out from the IC tag 5b of the tagged diaper 2 in the diaper package 31 and transmitted to the station PC 712, and the station PC 712 confirms whether the count of serial numbers which are read out is the normal quantity (five).

If it is confirmed that the count is not the normal quantity, the station PC 712 gives a report of abnormality to the operator. On the other hand, if it is confirmed that the count is the normal quantity, the gate type reader/writer 716 writes the date and time when the package inspection step is executed (i.e., the date and time when the tagged package 3 passes the downstream-side the gate type reader/writer 716), as shown in FIGS. 14B and 15B, to the IC tags 5b and 5c of the tagged diaper 2 and the tagged package 3, respectively.

In the inspection station 702, a packing step is executed in which twelve tagged packages 3 are packed in the packing box 41 to manufacture the tagged packing box 4. The operation in the packing step is the same as that of the above packaging step except that a plurality of tagged packages 3 are packed in the packing box 41; as such, discussion on a specific operation will be omitted.

To the packing box 41, the above IC tag 5d is adhered in advance in a step previous to the packing step. In the IC tag 5d, as shown in FIG. 16A, a serial number of the packing box 41 is stored in advance.

In the packing step, when the tagged packing box 4 passes the downstream-side gate type reader/writer 716, as shown in FIGS. 14B and 15B, the execution date and time of the packing step and the serial number of the tagged packing box 4 are stored in the IC tag 5b of the tagged diaper 2 and the IC tag 5c of the tagged package 3, and on the other hand, as shown in FIG. 16A, the execution date and time of the packing step, the serial numbers of a plurality of the tagged packages 3 contained in the tagged packing box 4 and the serial numbers of a plurality of tagged diapers 2 contained in the tagged package 3 are stored in the IC tag 5d of the tagged packing box 4.

Further, in the inspection station 702 executed is a packing inspection step of inspecting if a normal number of tagged packages 3 are packed in the packing box 41. Though the procedure of the packing inspection step will not be discussed as it is the same as the above package inspection step (see FIG. 8), when the packing inspection step is executed, as shown in FIGS. 14B, 15B and 16B, the execution date and time of the packing inspection step is additionally stored in the IC tags 5b to 5d.

The product database 91 which is updated in accordance with the steps in the above inspection station 702, as shown in FIG. 17B, becomes one where the execution dates and times of the package inspection step, the packing step and the packing inspection step and the serial number of the tagged packing box 4 (packing box serial No. in FIG. 17B) are added thereto. In FIG. 17B, data items other than the above data items are not shown. As the information to be stored in the IC tags 5b to 5d in the inspection station 702, besides the above items, an inspector name, an inspecting device which is used and the like are listed.

Figure 9:
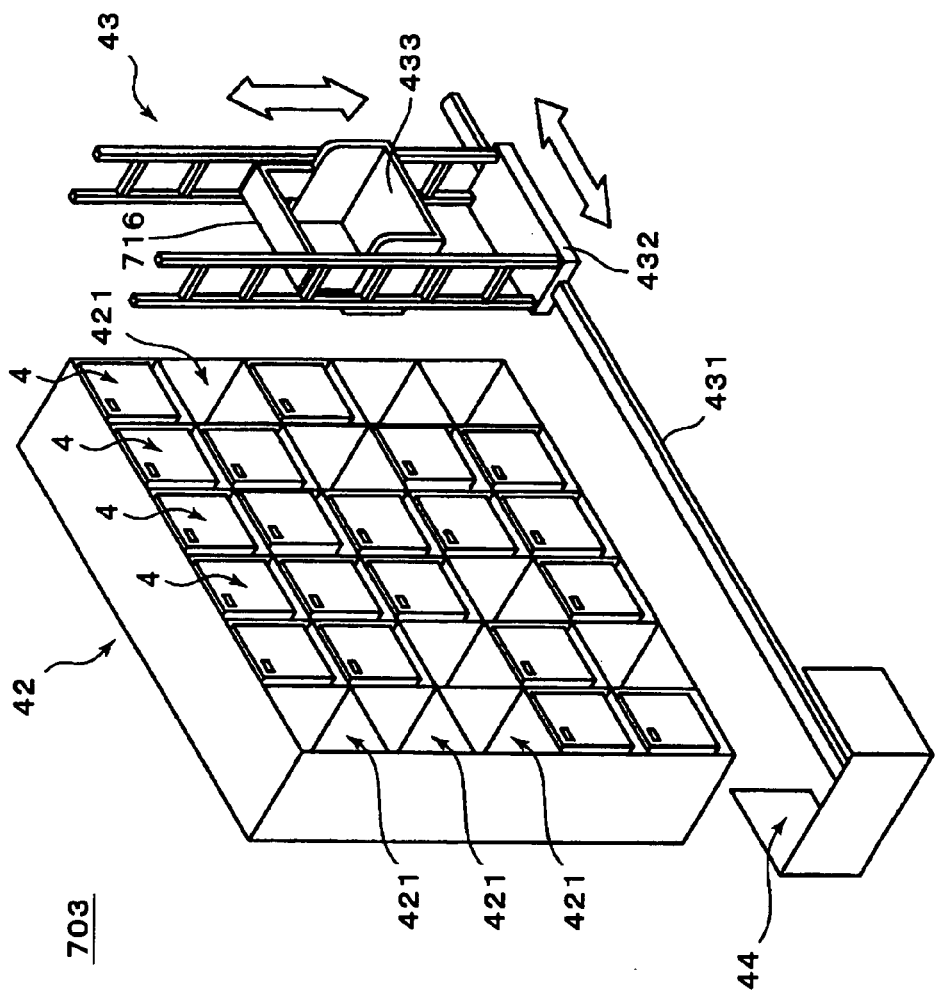
FIG. 9 is a perspective view showing a storage station.
Figure 10:
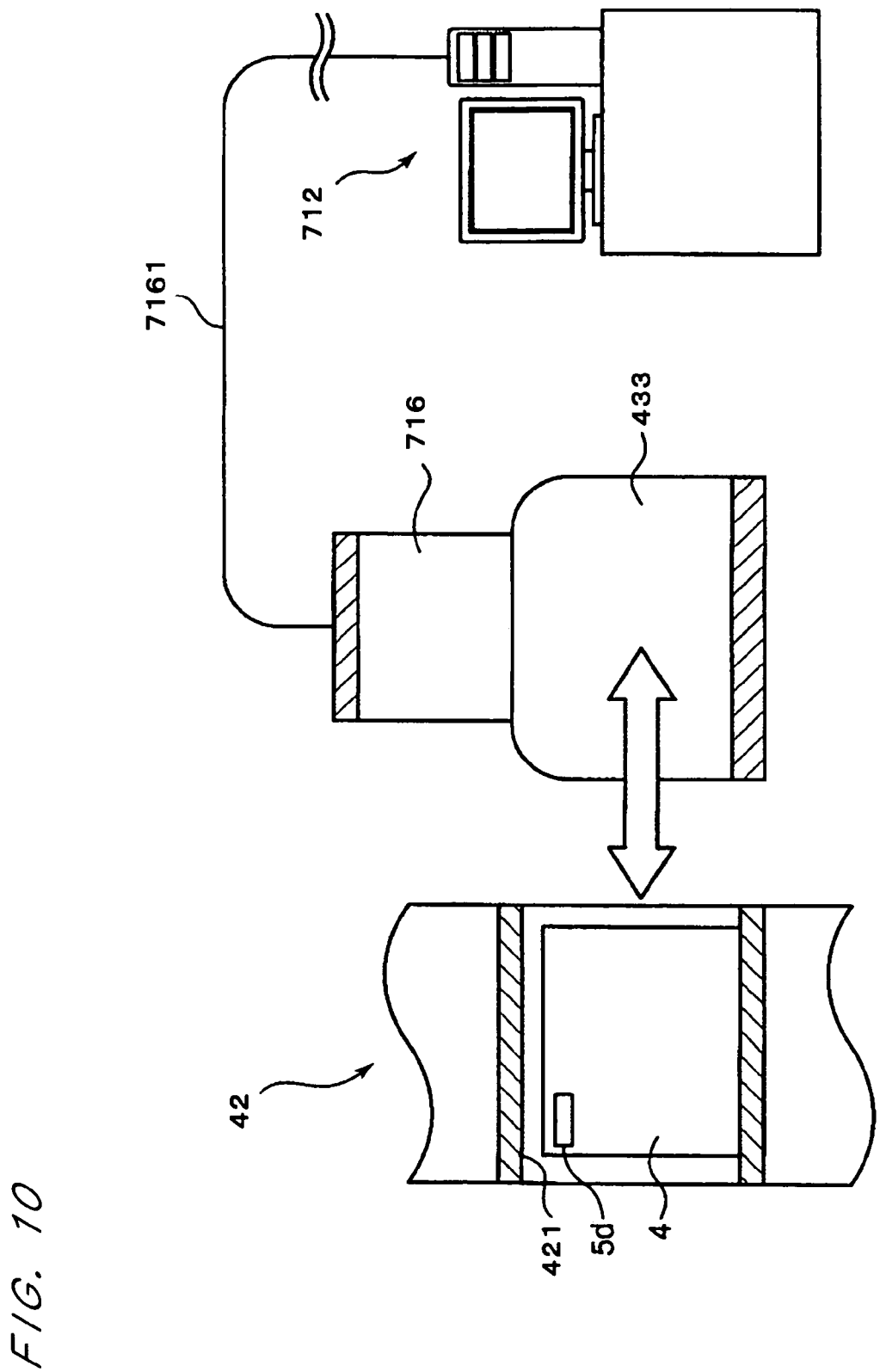
FIG. 10 is an enlarged view showing part of the storage station.

FIG. 9 is a perspective view showing part of the storage station 703. FIG. 10 is an enlarged view showing part of the storage station 703. In the storage station 703, for example, a storage step where the tagged packing box 4 is stored or retrieved is executed. As shown in FIGS. 9 and 10, in the storage station 703, a storage shelf 42 and a stacker crane 43 which puts the tagged packing box 4 into the storage shelf 42 or takes it out of the storage shelf 42 are provided.

In the storage shelf 42, a plurality of containing chambers 421 each of which is capable of containing the tagged packing box 4 are arranged in one row in depth direction and multiple rows in width and height directions. The containing chamber 421 is open in the depth direction of the storage shelf 42.

The stacker crane 43 comprises a rack 433 which is movable in a vertical direction over a slider 432 which is slidable along a rail 431 provided along the width direction of the storage shelf 42 on one side of openings of the containing chamber 421, and transfers the tagged packing box 4 placed on the rack 433 between a storage and retrieval station 44 provided beside the storage shelf 42 and a specified containing chamber 421.

Over the rack 433, the gate type reader/writer 716 is hung across and this gate type reader/writer 716 reads information out from and writes information to the respective IC tags 5d, 5c and 5b of the tagged packing box 4 placed on the rack 433, the tagged package 3 packed in the tagged packing box 4 and the tagged diaper 2, respectively. As shown in FIG. 10, the gate type reader/writer 716 can have communication with the station PC 712 through the cable 7161.

In the storage station 703, when the tagged packing box 4 is first put on the rack 433, as shown in FIGS. 14C, 15C and 16C, the date and time of that point is written and stored in the IC tags 5b to 5d as storing date and time, and when the tagged packing box 4 is put on the rack 433 again, the date and time of that point is written and stored in the IC tags 5b to 5d as retrieving date and time. When the tagged packing box 4 is first put on the rack 433, check on the process information on the previous step is made but this check is the same operation as discussed above and will not be discussed here.

If the tagged packing box 4 is put on the rack 433 third time or further (the tagged packing box 4 on which the storing date and time and the retrieving date and time are already stored in the IC tags 5b to 5d is stored again or the tagged packing box 4 which has been stored again is retrieved again), the older one of the storing date and time and the retrieving date and time is updated with the present date and time in the station PC 712. It is therefore possible to manage the case where the tagged packing box 4 is stored or retrieved again since the storing date and time is updated when it is stored again and the retrieving date and time is updated when it is retrieved again.

In the storage station 703, the storing date and time or the retrieving date and time is written to the IC tags 5b to 5d while the information of the IC tag 5b which includes the storing date and time or the retrieving date and time is read out and transmitted to the host computer 715, and the product database 91 is thereby updated. Specifically, when the storing step and the retrieving step are finished, the product database 91 is updated to one where the dates and times when the storing step and the retrieving step are executed are added thereto, as shown in FIG. 17C.

In the storage station 703, since a plurality of tagged packing boxes 4 are stored, being aligned, in the storage shelf 42, the handy type reader/writer 717 of FIG. 11 is especially suitable to check the respective contents of the tagged packing boxes 4. Since the handy type reader/writer 717 can read the information stored in the IC tag 5 and display it on the display panel 717a when its antenna provided on its top is brought nearer to the IC tag 5, it is possible for the operator in the storage station 703 to quickly check the content of the diaper product such as the tagged packing box 4 on hand. Further, by checking the storing date and time of the tagged packing box 4, it becomes possible to perform an FIFO (first-in-first-out) management of the stored tagged packing boxes 4.

Figure 12:
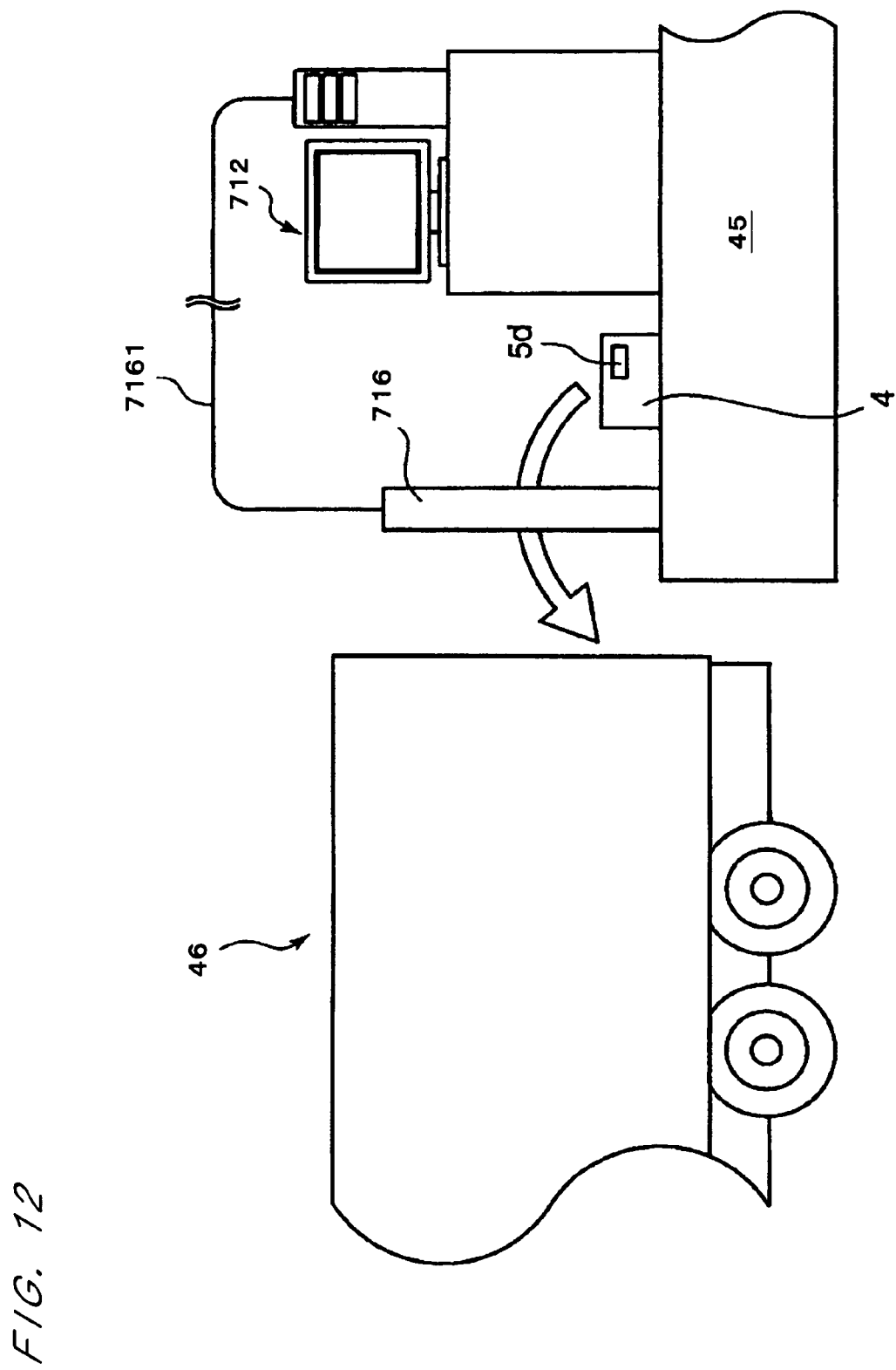
FIG. 12 is a view showing a shipping station.

FIG. 12 is a view showing a shipping terminal 45 which is one example of the shipping station 704. As shown in FIG. 12, in the shipping station 704, for example, a shipping step where the tagged packing box 4 transferred to the shipping terminal 45 is loaded onto a truck 46 for shipment is executed. Specifically, in the shipping terminal 45 for arrival and departure of the truck 46, the gate type reader/writer 716 is provided, which can have communication with the station PC 712 through the cable 7161.

In the shipping station 704, the tagged packing box 4 is loaded onto the truck 46 through the gate type reader/writer 716. When the tagged packing box 4 passes the gate type reader/writer 716, the above-discussed check on the process information on the previous step is made and the gate type reader/writer 716 writes and stores the execution date and time of the shipping step (i.e., shipping date and time) and the destination prefecture (e.g., Kanagawa Prefecture) to the IC tags 5b to 5d as shown in FIGS. 14D, 15D and 16D. The check on the process information on the previous step is the same operation as discussed above and will not be discussed here.

In the shipping terminal 45, the shipping date and time and the destination are written to the IC tags 5b to 5d while the information of the IC tag 5b which includes the shipping date and time and the destination is read out and transmitted to the host computer 715, and the product database 91 is thereby updated. Specifically, when the shipping step is finished, the product database 91 is updated to one where the shipping date and time and the destination prefecture are added thereto, as shown in FIG. 17D.

Though the gate type reader/writer 716 is provided in the shipping terminal 45 in FIG. 12, the gate type reader/writer 716 may be provided on, for example, a loading port of the truck 46. In this case, a constituent element for mutual radio communication is provided in the gate type reader/writer 716 and the station PC 712.

Figure 13:
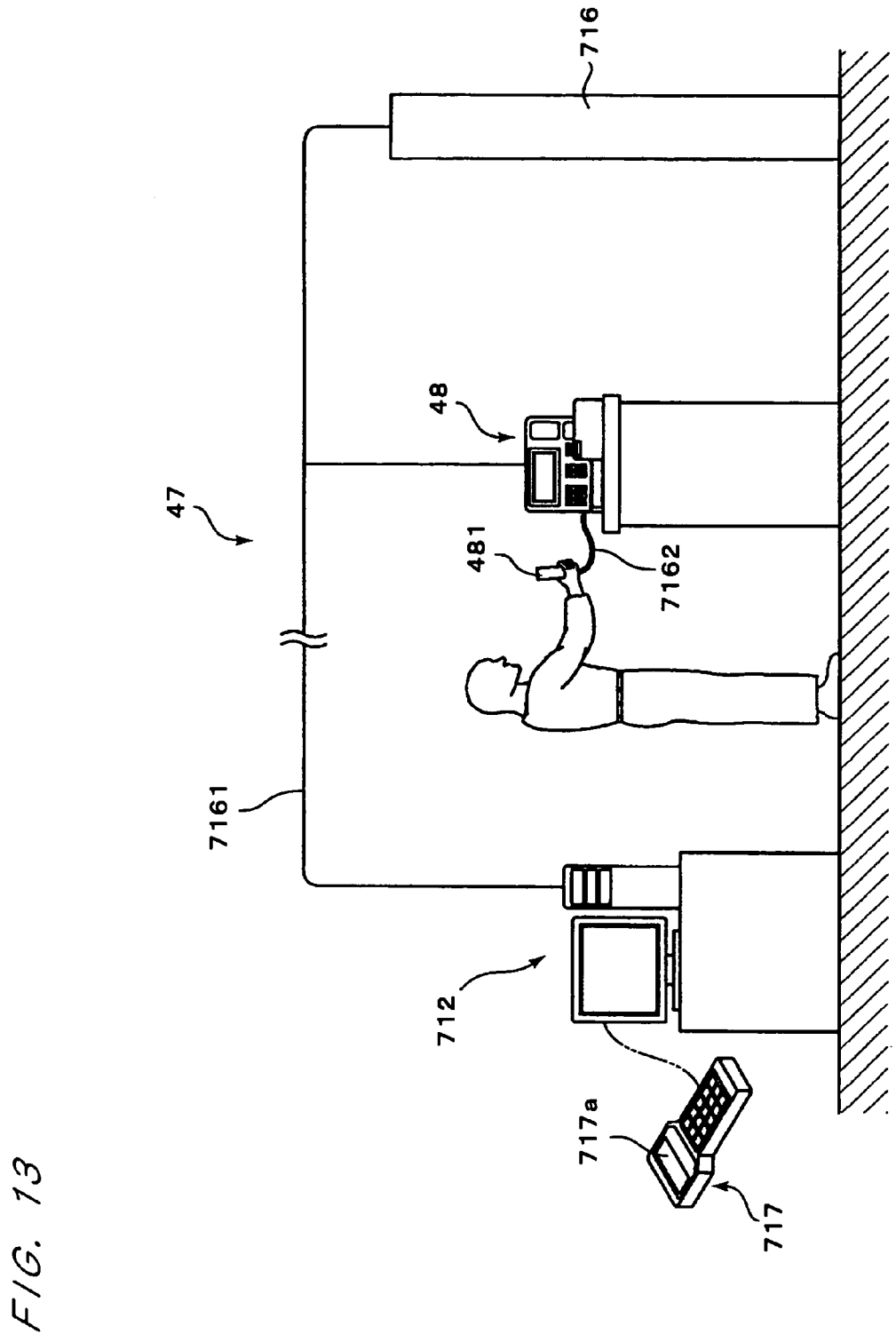
FIG. 13 is a view showing a dealer.

FIG. 13 is a view showing a dealer 47 which is one example of the sales station 705. As shown in FIG. 13, in the dealer 47, for example, a product check step of checking the tagged packing box 4 and a selling step of selling the tagged diapers 2 as a unit of the tagged package 3 are executed. In the dealer 47, a cash register 48 for settling accounts for products and the handy type reader/writer 717 are provided, and the cash register 48 can have communication with the station PC 712 through the cable 7161. The handy type reader/writer 717 can have communication with the station PC 712 through a cradle (not shown). In FIG. 13, the gate type reader/writer 716 discussed later is also shown.

In the product check step, by bringing the handy type reader/writer 717 nearer to the tagged packing box 4, the information on the delivered diaper product is read out from the IC tags 5b to 5d and transmitted to the station PC 712, and in the station PC 712, a confirmation is made on whether the diaper product is a product which should be supplied or not. Further, in the product check step, the handy type reader/writer 717 writes and stores the date and time when the product check step is executed (i.e., the product-checking date and time) and the dealer name to the IC tags 5b to 5d as shown in FIGS. 14E, 15E and 16E.

On the other hand, in the selling step, when a buyer takes the tagged diapers 2 as a unit of the tagged package 3 displayed in the shop to the cash register 48, the information stored in each IC tags 5b and 5c is read out by bringing a handy type reader/writer 481 connected to the cash register 48 through the cable 7162 nearer to the tagged package 3 while the date and time when the selling step is executed (i.e., selling date and time) is written and stored into the IC tags 5b and 5c as shown in FIGS. 14E and 15E.

Figures 17E, 18:
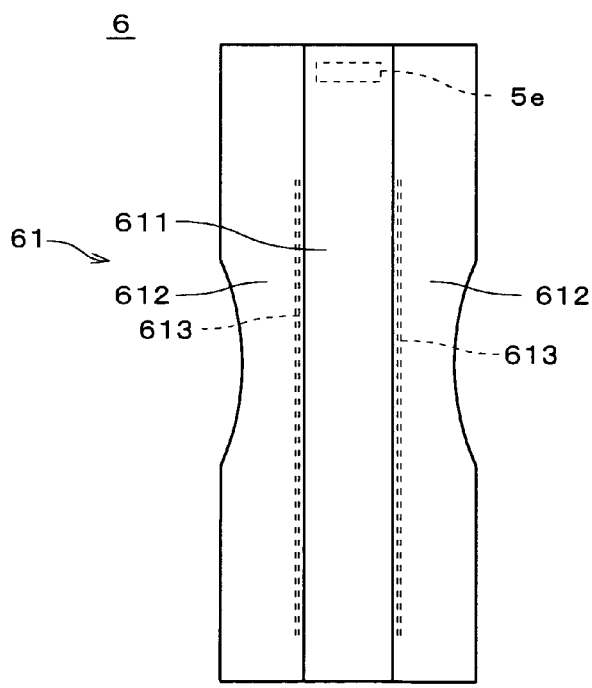
FIG. 17E is a view showing a product database.
FIG. 18 is a plan view showing a tagged pad in accordance with the preferred embodiment of the present invention.

The information read out from the IC tags 5b and 5c by the handy type reader/writer 481 is transmitted to the cash register 48, and in the cash register 48, a price of the tagged package 3 is displayed for the buyer. In the dealer 47, the product-checking date and time and the dealer name or the selling date and time are written to each IC tags 5b to 5d while the information of the IC tag 5b which includes the product-checking date and time, the dealer name and the selling date and time is read out and transmitted to the host computer 715 and the product database 91 is thereby updated. Specifically, when the product check step and the selling step are finished, the product database 91 is updated to one where the date and time when the product check step is executed (i.e., the product-checking date and time), the dealer name and the date and time when the selling step is executed (i.e., the selling date and time) are added thereto, as shown in FIG. 17E.

Though the handy type reader/writer 717 or 481 or the cash register 48 displays the price of the diaper product and writes the information to and reads the information out from the IC tags 5b and 5c in the above discussion, the writing and reading operation is not limited to this, but the gate type reader/writer 716 which is provided at a doorway of the dealer 47 and connected to the station PC 712 performs this operation.

In this case, by taking the delivered tagged packing box 4 in the shop through the gate type reader/writer 716, the above product check step is executed. When the buyer takes the tagged package 3 out of the shop, the information on the tagged package 3 is read out from the IC tags 5b and 5c to calculate the price and the price is charged separately to the buyer, to execute the selling step. In the above case where the selling step is executed by using the gate type reader/writer 716, if the buyer carries an IC tag storing his personal ID and the like, it is possible to charge the price to a charging destination on the basis of the above personal ID later.

In the above-discussed product database 91, the various items of information are assembled, being associated with the serial number of the tagged diaper 2 (in other words, the data elements are made up with the serial number of the tagged diaper 2 as key information), however the data structure of the product database 91 is not limited to this but the items of information may be assembled, being associated with the serial number of the tagged core 1, the tagged package 3 or the tagged packing box 4.

As discussed above, since the tagged core 1 and the tagged diaper 2 have the IC tags 5a and 5b, respectively, even when the body sheet 111 or the whole of disposal diaper 21 is contracted by the elastic members 112 or 215, the serial number of the tagged core 1 or the tagged diaper 2 can be reliably read out through the antenna for radio communication. Since the tagged package 3 and the tagged packing box 4 have the IC tags 5c and 5d, respectively, regardless of which direction the tagged package 3 or the tagged packing box 4 faces, the serial number of the tagged package 3 or the tagged packing box 4 can be reliably read out through the antenna for radio communication. Thus, as to the diaper product having the IC tag 5, it is possible to specify an individual diaper product by reading its serial number from its IC tag 5.

Since the supply information management system 710 comprises the host computer 715, the product database 91 can be created, in which the serial number of the tagged diaper 2 associates with the process information on the processes executed for the tagged core 1, the tagged diaper 2, the tagged package 3 and the tagged packing box 4 on the basis of the information read out from the IC tags 5a to 5d by the reader/writer 711 (i.e., the gate type reader/writer 716 or the handy type reader/writer 717), and it is possible to perform a proper and easy management of the information on supply of the diaper products with the product database 91. Further, in the supply information management system 710, since the reader/writer 711 and the station PC 712 are provided in each of the stations 701 to 705 for manufacture, inspection, storage, shipment and sale of the diaper product, respectively, it is possible to perform a serial management of the information from manufacture to sale of the diaper product.

Therefore, if it turns out that the diaper product with any serial number has some problem, by referring to the product database 91, the process information on the processes executed for the diaper product with this serial number can be easily checked. In other words, in the supply information management system 710, it is possible to secure the traceability of the diaper products.

If the serial number of the diaper product on hand or the like is uncertain, the supply information management system 710 with the handy type reader/writer 717 makes it possible to read the serial number or the like on the spot without moving the diaper product.

The supply information management system 710 with the confirming part 720 can check if the processes for the diaper product are executed in the normal order on the basis of the information read out from the IC tag 5. As a result, it is possible to prevent supply of defective products.

With the structure in which the host computer 715 receives information through the internet 714, it is possible to provide the host computer 715 at a location distant from the stations 701 to 705. Though FIG. 5 shows the case where the reader/writer 711 and the station PC 712 are provided in each of the stations 701 to 705, in the supply information management system 710, the reader/writer 711 and the station PC 712 may be provided as necessary in any of the stations for performing at least one of the processes of manufacturing, inspecting, storing, shipping and selling.

Next, discussion will be made on a diaper product management system for managing information on supply and usage of the diaper products. The diaper product for which management is carried out by the diaper product management system includes an IC-tagged auxiliary absorbent pad of FIG. 18, i.e., an absorbent pad (hereinafter, referred to as "tagged pad") 6 and the tagged diaper 2 or the like to which the tagged pad 6 is attached, as well as the tagged core 1, the tagged diaper 2, the tagged package 3 and the tagged packing box 4 of FIGS. 1 to 4, respectively.

FIG. 18 is a plan view showing the tagged pad 6. The tagged pad 6 comprises an absorbent pad 61 for receiving an excrement from a wearer, which is attached inside the disposal diaper or the like (e.g., the disposal diaper 21 of the tagged diaper 2), and an IC tag 5e attached to the absorbent pad 61.

The absorbent pad 61 comprises a body part 611 having a form of hourglass, which is formed of two sheets (top sheet and back sheet) and a crushed pulp or the like sandwiched therebetween and a pair of side wall parts 612 provided on both sides of the body part 611 in its width direction, and two elastic members 613 extending in the longitudinal direction are adhered to the side wall parts 612, respectively.

Like the IC tags 5a to 5d, the IC tag 5e comprises an IC chip which is capable of storing various information, an antenna for radio communication which is connected to the IC chip and a control part for performing the encoding and decoding process of the information which are sent or received through the antenna. In the IC chip of the IC tag 5e, a serial number for discriminating the absorbent pad 61 from other absorbent pads and a product model type indicating the kind of the absorbent pad 61 are stored in advance. The serial number here refers to part of a sequence of signs such as numbers and characters other than the part indicating the product model type, which is stored in the IC chip. Like in the tagged diaper 2 or the like, in the tagged pad 6, even when the absorbent pad 61 is contracted by the elastic members 613, the serial number and the product model type of the tagged pad 6 can be reliably read out through the antenna for radio communication.

Also in each of the diaper products other than the tagged pad 6 dealt in the diaper product management system (i.e., the tagged core 1, the tagged diaper 2, the tagged package 3 and the tagged packing box 4), the serial number for specifying the individual diaper product and the product model type indicating the kind of diaper product are stored in the IC chip of each of the IC tags 5a to 5d in advance.

In the following discussion, the IC tags 5a to 5e are generally termed as an IC tag 5 if these IC tags are not distinguished from each other. In the IC tag 5 dealt in the diaper product management system, the serial number and the product model type stored in the IC chip can be read out through the antenna for radio communication. In the IC tag 5 dealt in the diaper product management system, however, no information is written to the IC chip thereof (though information may be written thereto).

Figure 19:
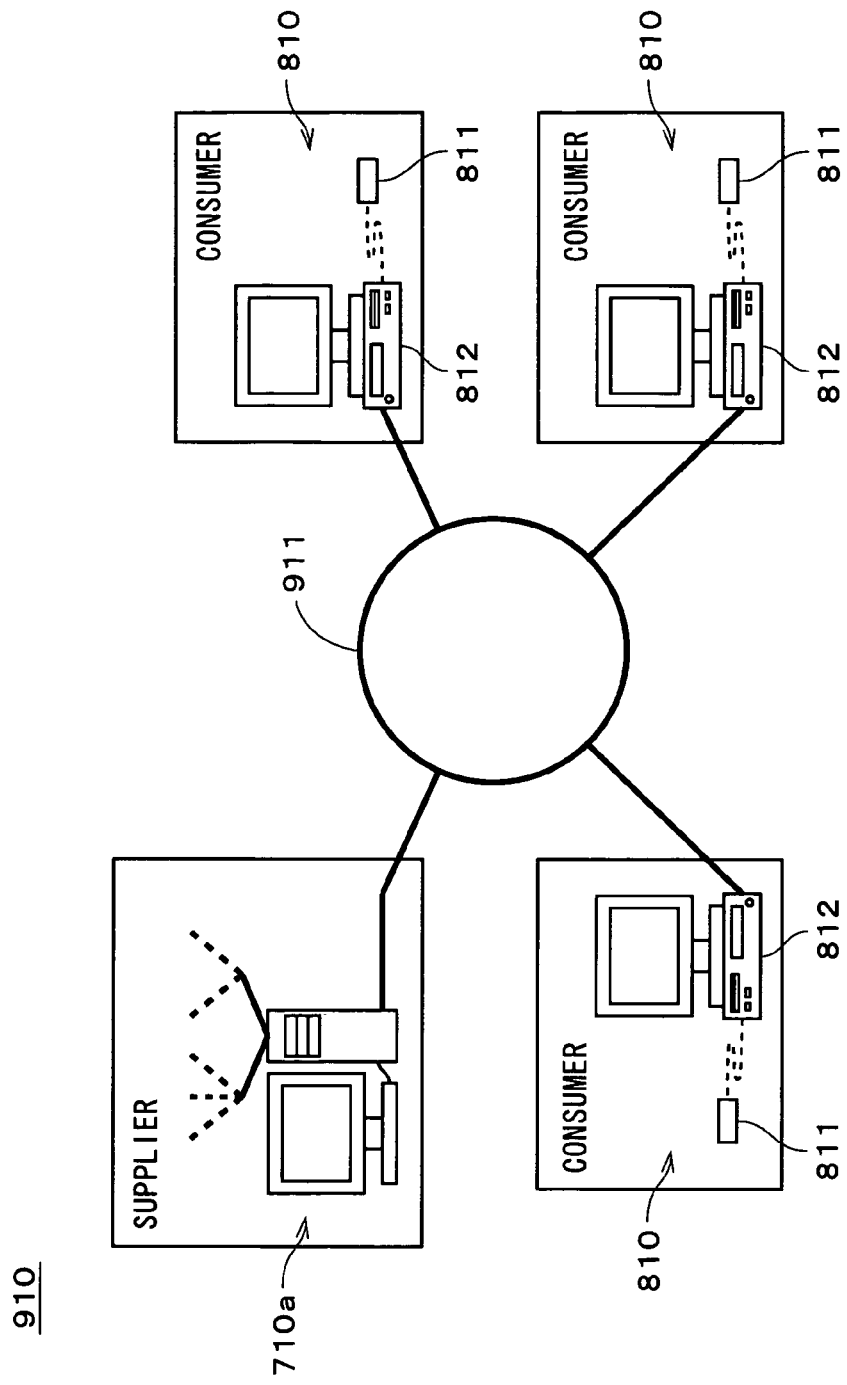
FIG. 19 is a view showing a constitution of a diaper product management system in accordance with the preferred embodiment of the present invention.

FIG. 19 is a view showing a constitution of a diaper product management system 910. As shown in FIG. 19, the diaper product management system 910 is constructed by connecting a supply information management system 710a provided and managed in a facility on a supplier side, which manufactures and sells diaper products, for managing the information on supply of the diaper products and a usage information management system 810 provided and managed in a facility on a consumer side (e.g., hospitals and care facilities such as nursing homes for the aged), which consumes a diaper product, for managing the information on usage of the diaper products, by a communication network 911. As the communication network 911, usually an internet is used but a special communication network such as WAN and LAN may be used.

Figure 20:
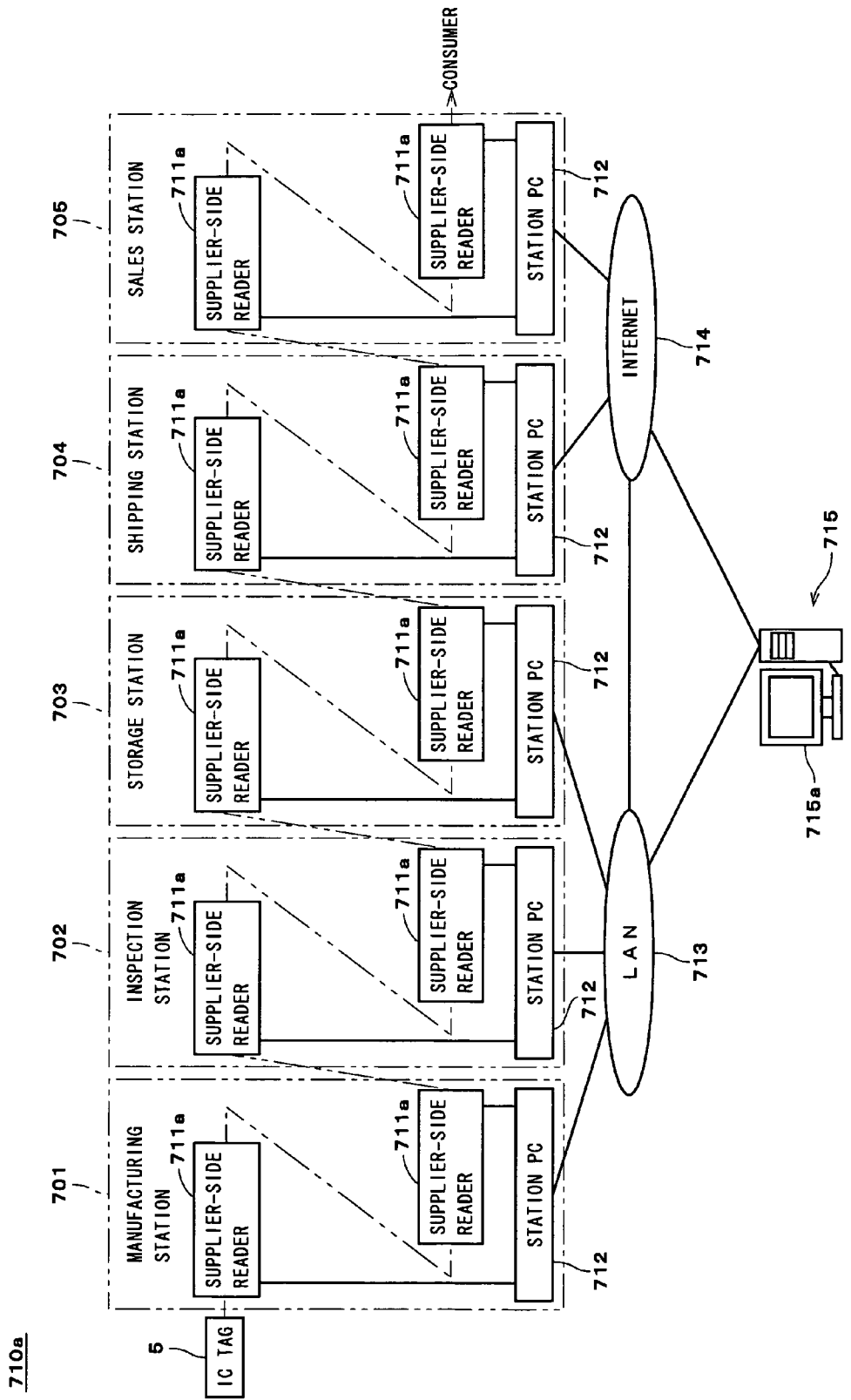
FIG. 20 is a view showing a constitution of the supply information management system.

FIG. 20 is a view showing a constitution of the supply information management system 710a. As shown in FIG. 20, in the supply information management system 710a, a supplier-side reader 711a which is a reading device for reading information from the IC chip of the IC tag 5 is provided, instead of the reader/writer 711 of the supply information management system 710. The other constituent elements are the same as those of FIG. 5 and are represented by the same signs in the following discussion. In the supply information management system 710a, the supplier-side reader 711a reads the serial number and the product model type of each diaper product, which are stored in advance, out from the IC chip of the diaper product provided with the IC tag 5 (e.g., the tagged core 1, the tagged diaper 2, the tagged package 3 or the tagged packing box 4 of FIGS. 1 to 4, respectively, and the tagged pad 6 of FIG. 18).

As shown in FIG. 19, the usage information management system 810 comprises a consumer-side reader 811 for reading the serial number and the product model type of the diaper product, which are stored in the IC chip in advance, out from the IC tag of the diaper product and a management device 812 connected to the consumer-side reader 811, and the management device 812 has constituent elements like in an ordinary computer, such as a CPU, a ROM and a RAM. The consumer-side reader 811 and the management device 812 may be connected with each other through a cable or the like, or through radio communication.

Figure 21:
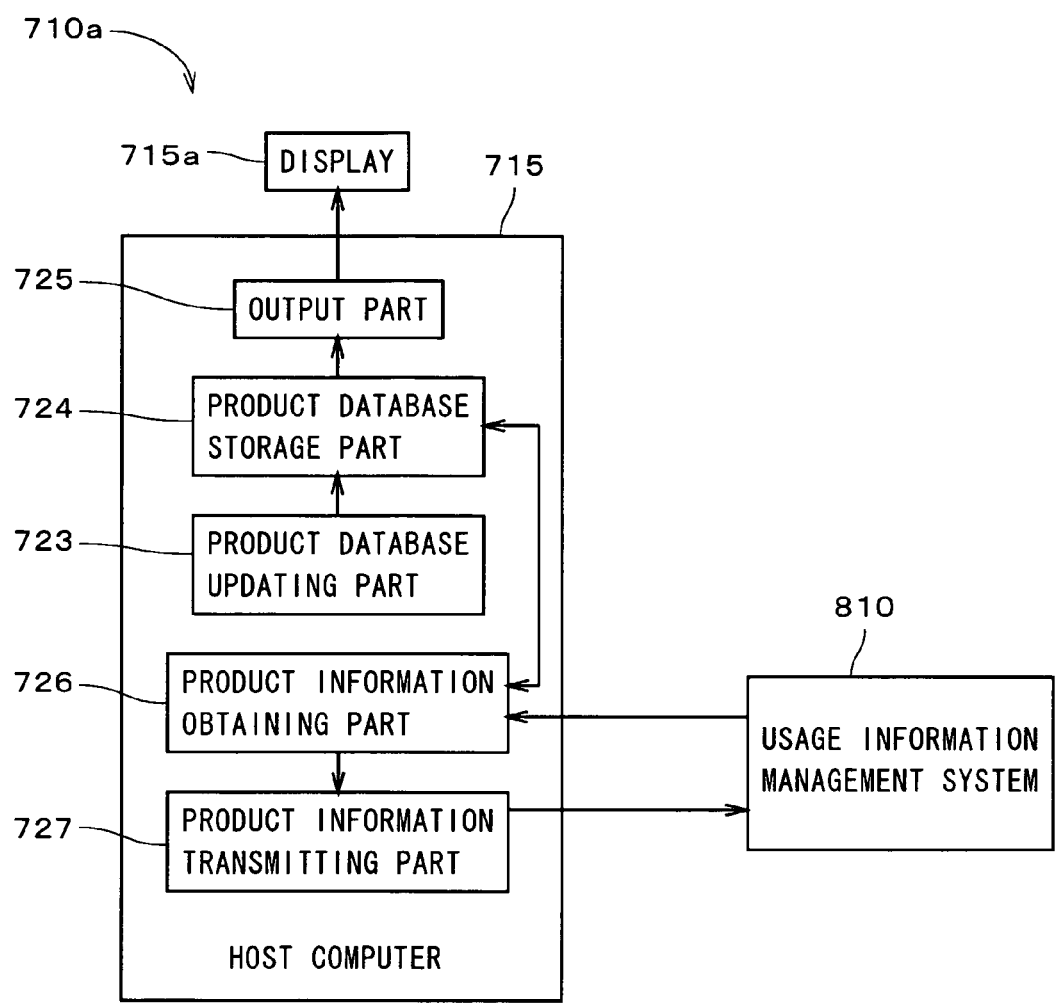
FIG. 21 is a block diagram showing some of functions of the supply information management system.

FIG. 21 is a block diagram showing some of functions of the supply information management system 710a. In the supply information management system 710a, a product database updating part 723, a product database storage part 724, an output part 725, a product information obtaining part 726 and a product information transmitting part 727 shown in FIG. 21 correspond to the functions implemented by the CPU and the like in the host computer 715. Other functions are the same as those in the supply information management system 710 of FIG. 6.

The product database updating part 723, the product database storage part 724 and the output part 725 shown in FIG. 21 have almost the same functions as those in the above-discussed supply information management system 710 (see FIG. 6), and the product database storage part 724 stores the product database 91 (see FIGS. 17A to 17E) which is a set of data elements each associating the serial number stored in the IC tag 5 of the diaper product in advance with the process information on the processes, such as manufacture, executed for the diaper product in the stations 701 to 705 (see FIG. 20). The output part 725 displays the product database 91 on the display 715*a*.

When one of the processes for the diaper product is executed in any one of the stations 701 to 705, the product database updating part 723 specifies the data element in the product database 91, which includes the serial number of the diaper product read out by the supplier-side reader 711*a* (see FIG. 20), and adds the process information on the process to the specified data element. In other words, the supply information management system 710*a* of FIG. 20 is a system where the constituent elements and operation for writing information to the IC tag 5 are omitted from the supply information management system 710 of FIG. 5.

In the supply information management system 710*a* with these constituent elements, like in the above-discussed supply information management system 710, it is possible to perform a proper and easy management of the information on supply of the diaper products.

The product information obtaining part 726 receives the serial number of the diaper product transmitted from the usage information management system 810 through the communication network 911 (see FIG. 19) to specify the data element including the serial number in the product database 91 stored in the product database storage part 724 and obtains values of predetermined data items in the specified data element as product information. The product information transmitting part 727 transmits the product information obtained by the product information obtaining part 726 to the usage information management system 810 through the communication network 911.

Figure 22:
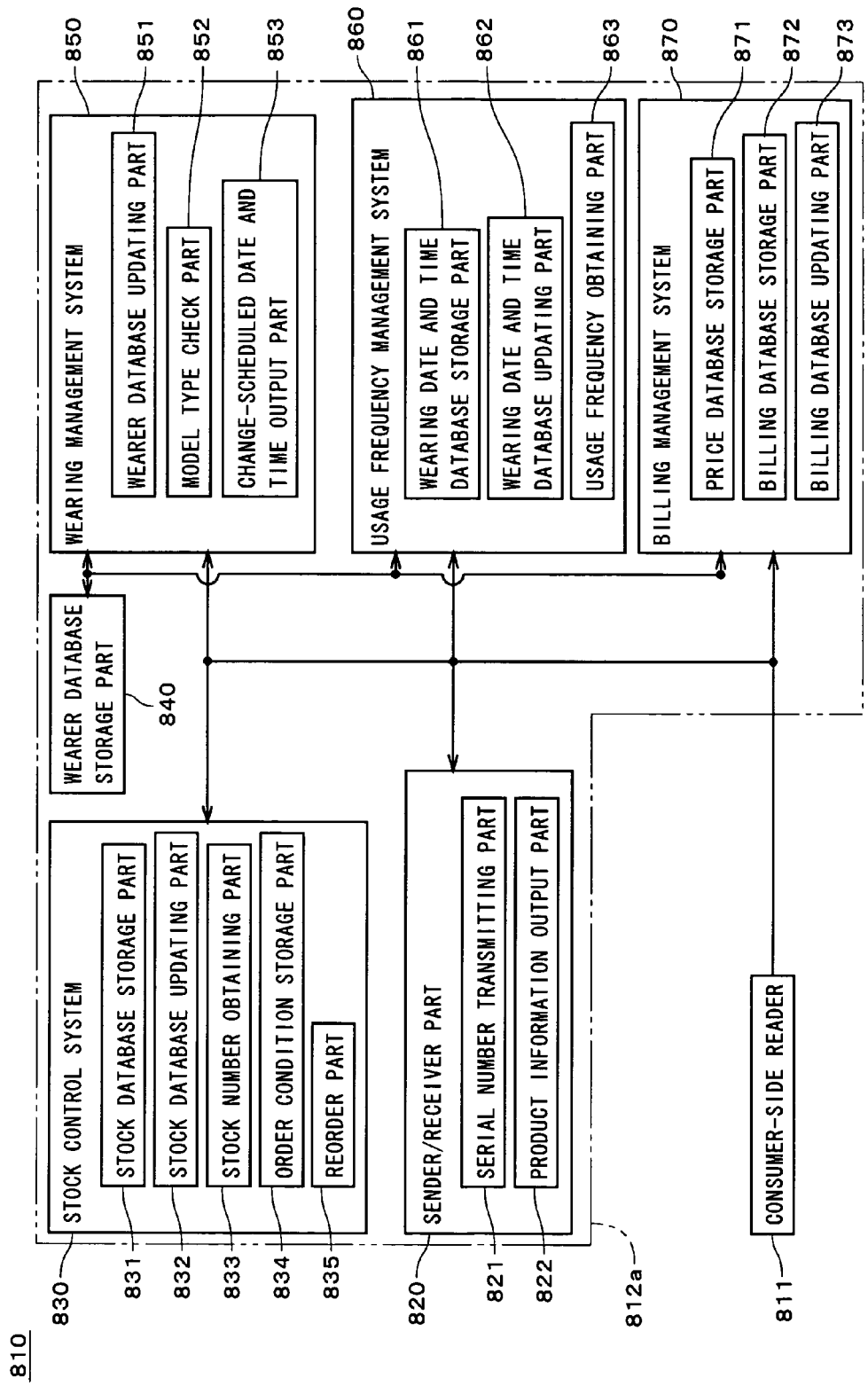
FIG. 22 is a block diagram showing functions of a usage information management system.

FIG. 22 is a block diagram showing functions of the usage information management system 810. The functions surrounded by the two-dot chain line 812*a* of FIG. 22, i.e., a sender/receiver part 820, a stock control system 830, a wearer database storage part 840, a wearing management system 850, a usage frequency management system 860 and a billing management system 870 correspond to functions implemented by the CPU, the memories and the like in the management device 812 (see FIG. 19).

The sender/receiver part 820, as one function implemented by the CPU and the like in the management device 812, has a serial number transmitting part 821 and a product information output part 822. The serial number transmitting part 821 transmits the serial number of the diaper product read out by the consumer-side reader 811 to the host computer 715 (see FIG. 21) in the supply information management system 710*a* through the communication network 911. The product information output part 822 receives the product information transmitted by the product information transmitting part 727 (see FIG. 21) in the supply information management system 710*a* and outputs it to an output device such as a display.

Functions of constituent elements other than the sender/receiver part 820 will be discussed later.

In the diaper product management system 910 of FIG. 19, if it turns out in the facilities on the consumer side such as care facilities that the diaper product has some problem (for example, the tagged diaper 2 has an absorbing power smaller than usual), the serial number of the diaper product which has the problem (hereinafter, referred to as "defective product") is read out from its IC tag 5 by the consumer-side reader 811 of the usage information management system 810 and transmitted to the sender/receiver part 820 in the management device 812 (see FIG. 22), and then the serial number is transmitted by the serial number transmitting part 821 in the sender/receiver part 820 to the host computer 715 in the supply information management system 710*a* (see FIG. 21) through the communication network 911.

In the supply information management system 710*a* of FIG. 21, the product information obtaining part 726 of the host computer 715 receives the serial number of the defective product transmitted from the serial number transmitting part 821 in the usage information management system 810, and the data element including the serial number is specified in the product database 91 and values in predetermined data items in the specified data element (e.g., "absorbent core serial No." and the execution date and time of "adhesion step" shown in FIG. 17A) are obtained as product information. The product information transmitting part 727 transmits the product information to the usage information management system 810 through the communication network 911 and the product information output part 822 in the sender/receiver part 820 receives the product information and outputs it on a display or the like. At the same time, in the supply information management system 710*a*, the output part 725 of the host computer 715 outputs the product information on the display 715*a* or the like.

This secures traceability of the diaper products on the supplier and consumer sides of the diaper products, and when a diaper product has some problem, it is possible to easily check the information to specify the material used for the defective product and the process information on the process performed for the defective product. As a result, on the supplier side, it is possible to easily search for the cause of the problem and quickly recall other diaper products manufactured at the same time as the defective product. On the consumer side, it is possible to check other diaper products manufactured at the same time as the defective product before use and discard any diaper products which are defective, instead of being used.

Next, the stock control system 830 in the usage information management system 810 will be discussed. As shown in FIG. 22, the stock control system 830 has a stock database storage part 831, a stock database updating part 832, a stock number obtaining part 833, a order condition storage part 834 and a reorder part 835 as functions implemented by the CPU, the memories and the like in the management device 812.

The stock database storage part 831 stores a stock database 92 of FIG. 23. As shown in FIG. 23, the stock database 92 is a set of data elements each associating the serial number of the diaper product which is delivered to the consumer-side facility (e.g., the tagged diaper 2 and the tagged pad 6 shown in FIGS. 2 and 18, respectively) with the product model type and the state of usage (i.e., whether used or not) of the diaper product.

The stock database updating part 832 of FIG. 22 specifies the data element including the serial number of the diaper product read out by the consumer-side reader 811, in the stock database 92 stored in the stock database storage part 831, and updates it. The stock number obtaining part 833 obtains the number of stock of diaper products corresponding to each product model type on the basis of the stock database 92.

The order condition storage part 834 stores the stock threshold value (the minimum stock number of products which should be secured) and the number of products to be reordered, corresponding to each of a plurality of product model types of the diaper products, in advance. The reorder part 835 reorders the diaper product corresponding to each product model type to a selling agency of the diaper product as necessary on the basis of the stock number obtained by the stock number obtaining part 833.

On the consumer side, when a caregiver puts a diaper product (e.g., the tagged diaper 2 of FIG. 2) on a wearer (i.e., caregiver), the serial number is read out from the IC tag 5 of the diaper product to be put on by the handy type consumer-side reader 811 that the caregiver carries with him and transmitted to the stock database updating part 832 in the stock control system 830.

The stock database updating part 832 specifies one data element in the stock database 92 (see FIG. 23), which includes the serial number transmitted from the consumer-side reader 811, and updates the value of the data item indicating the state of usage in the specified data element, from "unused" to "used".

In the stock control system 830 of the usage information management system 810, the stock number obtaining part 833 selects one of a plurality of product model types of the diaper products, specifies all the data elements in the stock database 92, which include the selected product model type and the data item indicating the state of usage, whose value is "unused", and obtains the number of specified data elements as the stock number for the diaper product corresponding to the selected product model type. In the stock control system 830, the stock number obtaining part 833 obtains the stock number of the diaper product corresponding to each of a plurality of product model types.

Further, in the stock control system 830, the reorder part 835 continuously compares the stock number for the diaper product corresponding to each product model type, which is obtained by the stock number obtaining part 833, with the stock threshold value stored in the order condition storage part 834 in advance. When the stock number for the diaper product corresponding to any one product model type becomes smaller than the stock threshold value, the reorder part 835 transmits order information for reorder to the selling agency of the diaper product corresponding to the product model type through the communication network 911. The order information includes information specifying the consumer-side facility, the product model type of the diaper product whose stock number becomes smaller than the stock threshold value, the number of products to be reordered, corresponding to the product model type, which is stored in the order condition storage part 834 in advance, and the like.

When the diaper products are delivered from the selling agency in accordance with the order information, the serial number and the product model type of each of the delivered diaper products (e.g., the tagged diapers 2) is read out from the IC tag 5 of the diaper product by the consumer-side reader 811 and added to the stock database 92 as a new data element by the stock database updating part 832. At this time, the value of the data item indicating the state of usage in the added data element is made "unused".

Thus, in the stock control system 830 of the usage information management system 810, by managing the state of usage of each diaper product in the stock database 92, it is possible to easily achieve stock control of the diaper products and reduce a burden in stock control operation in the consumer-side facilities such as care facilities where many kinds of diaper products are used in volume every day. Since the reorder part 835 automatically reorders the diaper products in accordance with the stock number for the diaper product, it is also possible to reduce a burden in order operation.

Further, the tagged diaper 2 on delivery is usually packaged in the diaper package 31 and the like such that the IC tag 5b cannot be visually recognized but the consumer-side reader 811 can read information from a plurality of IC tags 5b of a plurality of tagged diapers 2 in a noncontact manner at almost the same time. It is therefore possible to perform a proper and easy operation of updating the stock database 92 on delivery of the diaper product.

Next, the wearer database storage part 840 and the wearing management system 850 in the usage information management system 810 will be discussed. The wearer database storage part 840 stores a wearer database 93 shown in FIG. 24. The wearer database 93 is a database with a wearer identification number for discriminating one wearer of a diaper product from other wearers as key information. In the consumer-side facilities provided with the usage information management system 810, a wristband type IC tag in which the wearer identification number is stored in its IC chip in advance is distributed to each wearer and the wearer identification number can be read out by the consumer-side reader 811 that the caregiver carries with him. A reader for reading the wearer identification number from the wristband type IC tag of the wearer may be a device different from the consumer-side reader 811 which reads the information from the IC tag 5 of the diaper product. Another type of IC tag other than the wristband type may be given to each wearer, a bed of the wearer or the like, and alternatively a list which collectively presents wearer identification numbers of a plurality of wearers in such a format as can be read by a reading device, such as a bar code, may be distributed to each caregiver.

As shown in FIG. 24, the wearer database 93 is a set of data elements each associating the wearer identification number (not necessarily limited to combination of characters and numbers but may be only either numbers or characters) for discriminating one wearer of the diaper product from other wearers (in other words, for individually specifying a plurality of wearers of the diaper product) with an applicable model type which is a product model type of a diaper product to be put on a wearer corresponding to the wearer identification number, a latest wearing date and time when the diaper product is put on and a change interval of the diaper product. Each data element in the wearer database 93 includes pieces of information indicating the applicable model type, the latest wearing date and time and the change interval of each of the tagged diaper 2 and the tagged pad 6 (a diaper model type, a diaper latest wearing date and time, a diaper change interval, a pad model type, a pad latest wearing date and time and a pad change interval in FIG. 24).

As shown in FIG. 22, the wearing management system 850 has a wearer database updating part 851, a model type check part 852 and a change-scheduled date and time output part 853 as functions implemented by the CPU and the like in the management device 812.

The wearer database updating part 851 specifies the data element including the wearer identification number read out by the consumer-side reader 811 in the wearer database 93 stored in the wearer database storage part 840 and updates it. The model type check part 852 checks the product model type of the diaper product to be put on with the applicable model type in the wearer database 93 when the diaper product is put on the wearer. The change-scheduled date and time output part 853 outputs a next change-scheduled date and time of the diaper product for each wearer.

In the consumer-side facilities, when a caregiver puts the tagged diaper 2 or the tagged pad 6 on a wearer, first, the wearer identification number is read out from the wristband type IC tag of the wearer by the consumer-side reader 811 that the caregiver carries with him and transmitted to the model type check part 852 in the wearing management system 850. Subsequently, the model type check part 852 specifies one data element in the wearer database 93 (see FIG. 24), which includes the wearer identification number transmitted from the consumer-side reader 811, and the applicable model type (the diaper model type and the pad model type in FIG. 24) in the specified data element is transmitted to the consumer-side reader 811 and displayed thereon.

Next, the caregiver selects the diaper product having the product model type to be put on, on the basis of the applicable model type displayed on the consumer-side reader 811, and the consumer-side reader 811 reads the product model type from the IC tag 5 of the diaper product and transmits it to the model type check part 852. The model type check part 852 checks the applicable model type of the data element specified on the basis of the wearer identification number with the product model type read out from the diaper product, and when the applicable model type and the product model type are coincident with each other, this coincidence is transmitted to the consumer-side reader 811 and displayed thereon and when not coincident, the applicable model type is displayed again on the consumer-side reader 811.

It is thereby possible to surely put the diaper product corresponding to an appropriate product model type on the wearer and perform an appropriate excretion care. Even in the consumer-side facilities such as care facilities where the operation of changing the diaper products for many wearers is required, it is possible to perform an easy operation of changing the diaper product and reduce a burden in changing the diaper product.

Even if the wearer wears the diaper product corresponding to the applicable model type, however, in a case where the body condition of the wearer changes (for example, the wearer gets thinner due to change in health condition), there is a possibility that a gap made between the wearer and the diaper product causes a leakage of urine or the like. If a change of the applicable model type of the diaper product to be put on the wearer is needed thus, the caregiver selects a diaper product of appropriate product model type which is different from the present applicable model type and the product model type of this diaper product (the product model type after changing) is read out from the IC tag 5 by the consumer-side reader 811.

The changed product model type which is read out by the consumer-side reader 811 is transmitted, together with the wearer identification number which is also read out by the consumer-side reader 811, to the wearer database updating part 851 in the wearing management system 850. Then, the wearer database updating part 851 specifies the data element including the wearer identification number in the wearer database 93 and updates the value of the applicable model type in the specified data element to the changed product model type which is transmitted from the consumer-side reader 811.

This makes it possible to easily and reliably record the change of the applicable model type when the change in the applicable model type of the diaper product for the wearer is needed. Additionally, caregivers other than the one who performs the operation of changing the applicable model type can be properly informed about the change of the applicable model type. As a result, if the applicable model type is changed, it is possible to surely put the diaper product corresponding to the appropriate product model type on the wearer and perform an appropriate excretion care. It is further possible to simplify the informing operation among the caregivers on the change of the applicable model type and reduce a burden in informing operation.

In the wearing management system 850, the wearer database updating part 851 updates the latest wearing date and time of the diaper product in the wearer database 93. In a case where the tagged diaper 2 is changed, for example, when a new tagged diaper 2 is put on a wearer, the wearer identification number is read out from the wristband type IC tag of the wearer by the consumer-side reader 811 and transmitted to the wearer database updating part 851.

Then, the wearer database updating part 851 specifies the data element including the wearer identification number in the wearer database 93 and updates the latest wearing date and time of the tagged diaper 2 (the diaper latest wearing date and time of FIG. 24) in the specified data element to the date and time when the new tagged diaper 2 is put on the wearer (exactly, the date and time when the wearer database updating part 851 receives the wearer identification number from the consumer-side reader 811). In the wearing management system 850, the update of the latest wearing date and time in the wearer database 93 may be performed at the same time as the check of the product model type of the diaper product or the change of the applicable model type.

When the latest wearing date and time of the tagged diaper 2 is updated, the change-scheduled date and time output part 853 obtains the next change-scheduled date and time of the tagged diaper 2 on the basis of the updated latest wearing date and time and the change interval of the tagged diaper 2 (the diaper change interval of FIG. 24) in the data element and outputs the change-scheduled date and time to a display device such as a display. At a point of time before the change-scheduled date and time by a predetermined time (for example, at a half hour before the change-scheduled date and time), the change-scheduled date and time output part 853 may give the caregivers a notice that the change-scheduled date and time is approaching.

In the wearing management system 850, in a case where the tagged pad 6 is changed for a wearer, like in the change of the tagged diaper 2, the wearer database updating part 851 updates the latest wearing date and time of the tagged pad 6 (the pad latest wearing date and time of FIG. 24) and the change-scheduled date and time output part 853 outputs a next change-scheduled date and time of the tagged pad 6 on the basis of the updated latest wearing date and time and the change interval of the tagged pad 6 (the pad change interval of FIG. 24). In a case where the tagged pad 6 and the tagged diaper 2 are changed at the same time, the latest wearing dates and times of these diaper products are updated and the respective next change-scheduled dates and times are outputted.

Thus, in the wearing management system 850, since the latest wearing date and time of the diaper product is recorded in the wearer database 93, it is possible to easily and reliably manage the change-scheduled date and time of the diaper product for each wearer. Further, in the wearing management system 850, on the basis of the wearer identification number and the product model type which are read out by the consumer-side reader 811 and the latest wearing date and time and the change interval of the product model type which are associated with the wearer identification number in the wearer database 93, the change-scheduled date and time output part 853 outputs a next change-scheduled date and time of the diaper product corresponding to the product model type. This makes it possible to easily and reliably manage the change-scheduled date and time of the diaper product and properly inform other caregivers about the latest wearing date and time and the change-scheduled date and time. As a result, it is possible to change the diaper product for the wearer at an appropriate interval and achieve an appropriate excretion care. It is also possible to simplify the informing operation among the caregivers on the change-scheduled date and time and reduce a burden in informing operation.

Next, the usage frequency management system 860 in the usage information management system 810 will be discussed. As shown in FIG. 22, the usage frequency management system 860 has a wearing date and time database storage part 861, a wearing date and time database updating part 862 and a usage frequency obtaining part 863 as functions implemented by the CPU, the memories and the like in the management device 812.

The wearing date and time database storage part 861 stores a wearing date and time database 94 shown in FIG. 25. As shown in FIG. 25, the wearing date and time database 94 is a set of data elements each associating a wearer identification number for a wearer of a diaper product and a product model type of the diaper product with wearing date and time when the diaper product is put on the wearer. In the data elements of FIG. 25, the product model type whose first character is "P" (e.g., "PS001") indicates the tagged pad 6 and the product model type whose first character is "D" (e.g., "DM001") indicates the tagged diaper 2. As shown in FIG. 25, in the wearing date and time database 94, a plurality of data elements include the product model types for the tagged diapers 2 and other data elements includes the product model types for the tagged pads 6.

Every time when a diaper product is put on a wearer, the wearing date and time database updating part 862 generates a new data element associating the wearing date and time of the diaper product with the product model type and the wearer identification number and adds the new data element to the wearing date and time database 94 stored in the wearing date and time database storage part 861. The usage frequency obtaining part 863 obtains the usage frequency of the diaper product for each wearer (in other words, the number of diaper products which are used during a predetermined period such as one week or one month) from the wearing date and time database 94.

In the consumer-side facilities, when a caregiver puts the tagged diaper 2 or the tagged pad 6 on a wearer, first, the wearer identification number and the product model type of the diaper product to be put on are read out by the consumer-side reader 811 and transmitted to the wearing date and time database updating part 862. Then, the wearing date and time database updating part 862 associates the wearer identification number and the product model type from the consumer-side reader 811 with the wearing date and time of the diaper product (exactly, the date and time when the wearing date and time database updating part 862 receives the wearer identification number and the product model type from the consumer-side reader 811) and adds this new data element to the wearing date and time database 94.

In the usage frequency management system 860, when the usage frequency obtaining part 863 obtains the usage frequency of the diaper product, first, all the data elements having the same wearer identification number and product model type as those designated by the caregiver or the like are specified in the wearing date and time database 94 by the usage frequency obtaining part 863. Then, on the basis of the wearing dates and times of the specified data elements, the number of diaper products corresponding to the designated product model type, which are used by a wearer corresponding to the designated wearer identification number in a predetermined period is obtained as usage frequency.

In the usage frequency obtaining part 863, if the caregiver or the like designates the product model types of a plurality of diaper products, e.g., the tagged diaper 2 and the tagged pad 6 (see FIGS. 2 and 18), the usage frequency of the tagged diaper 2 and that of the tagged pad 6 are individually obtained. If a plurality of wearer identification numbers are designated, the usage frequency of the diaper product for each wearer is obtained.

Even in the consumer-side facility such as a care facility where many kinds of diaper products are used for many wearers, it is possible to easily and accurately keep track of the usage frequency of the diaper product for each wearer by product model type. By analyzing the usage frequency of the diaper product, it is possible to improve the quality of excretion care such as adjustment of change interval of the tagged pad 6 or the tagged diaper 2 for each wearer and change of the applicable model type.

The usage frequency management system 860 may be provided and managed on a supplier side concerned with manufacture, sale and the like of a diaper product. In this case, the wearer identification number and the product model type read out by the consumer-side reader 811 are transmitted to the usage frequency management system 860 through the communication network 911, together with the information specifying a consumer-side facility.

The usage frequency of the diaper product obtained by the usage frequency obtaining part 863 can be used as a tool for planning of strategies on sales policy of the diaper products and development policy of new products on the supplier side. If the usage frequency of the tagged pad 6 is higher than that of the tagged diaper 2, for example, since one tagged diaper 2 can be used for longer time, development of diapers with high breathability and presentation thereof to the supplier side will be performed, or the number of tagged diapers 2 to be packed in one tagged package 3 can be determined in accordance with the number of tagged diapers 2 which are used for one day or one week.

Next, the billing management system 870 in the usage information management system 810 will be discussed. As shown in FIG. 22, the billing management system 870 has a price database storage part 871, a billing database storage part 872 and a billing database updating part 873 as functions implemented by the CPU, the memories and the like in the management device 812.

The price database storage part 871 stores a price database 95 shown in FIG. 26. As shown in FIG. 26, the price database 95 is a set of data elements each associating a product model type of a diaper product with a price thereof. The billing database storage part 872 stores a billing database 96 shown in FIG. 27. As shown in FIG. 27, the billing database 96 is a set of data elements each associating a wearer identification number for a wearer of a diaper product with a self-pay ratio for the cost of use of diaper products and a billing amount for a predetermined period (in other words, a self-pay amount for the cost of the diaper products used for the predetermined period). The billing database updating part 873 updates the billing amount of a wearer in the billing database 96 every time when a diaper product is put on the wearer.

In the consumer-side facilities, when a caregiver puts the tagged diaper 2 or the tagged pad 6 on a wearer, first, the product model type of a diaper product to be put on and the wearer identification number of the wearer who puts on the diaper product are read out by the consumer-side reader 811 and transmitted to the billing database updating part 873.

Subsequently, the billing database updating part 873 specifies one data element in the price database 95, which includes the product model type transmitted from the consumer-side reader 811, and the price of the diaper product in the specified data element is acquired. Further, the data element including the wearer identification number from the consumer-side reader 811 is specified in the billing database 96 and the self-pay ratio in the specified data element is obtained.

Then, the billing database updating part 873 adds the product of the price of the diaper product and the self-pay ratio which are acquired as discussed above to the billing amount in the specified data element in the billing database 96. In other words, the value of the billing amount in the specified data element in the billing database 96 is updated to an account obtained by adding the product of the price of the diaper product which is put on and the self-pay ratio to the billing amount at the point of time when the data element is specified.

Even in the consumer-side facility such as a care facility where many kinds of diaper products are used for many wearers, it is possible to easily and accurately perform a billing management on usage of the diaper products for each wearer and reduce a burden in billing management. In facilities where the self-pay ratio is 100% for all the wearers (for example, where there is no one who is aided by the nursing care insurance or the like), the data item indicating the self-pay ratio may be omitted from the billing database 96. In this case, in the billing database updating part 873, the price of the diaper product to be put on is added to the billing amount without any calculation.

As discussed above, in the diaper product management system 910 which has a construction where the supply information management system 710*a* provided and managed on the supplier side of the diaper products and the usage information management system 810 provided and managed on the consumer side of the diaper products are connected by the communication network 911, it is possible to perform a proper and easy management of the information on supply and usage of the diaper products and secure the traceability of the diaper products.

In the usage information management system 810, it is possible to perform a proper and easy management of the information on usage of the diaper products. In the supply information management system 710*a*, it is possible to perform a proper and easy management of the information on supply of the diaper products and secure the traceability of the diaper products. Further, the supply information management system 710*a* produces the same effect even if it functions independently from the usage information management system 810.

Figure 28:
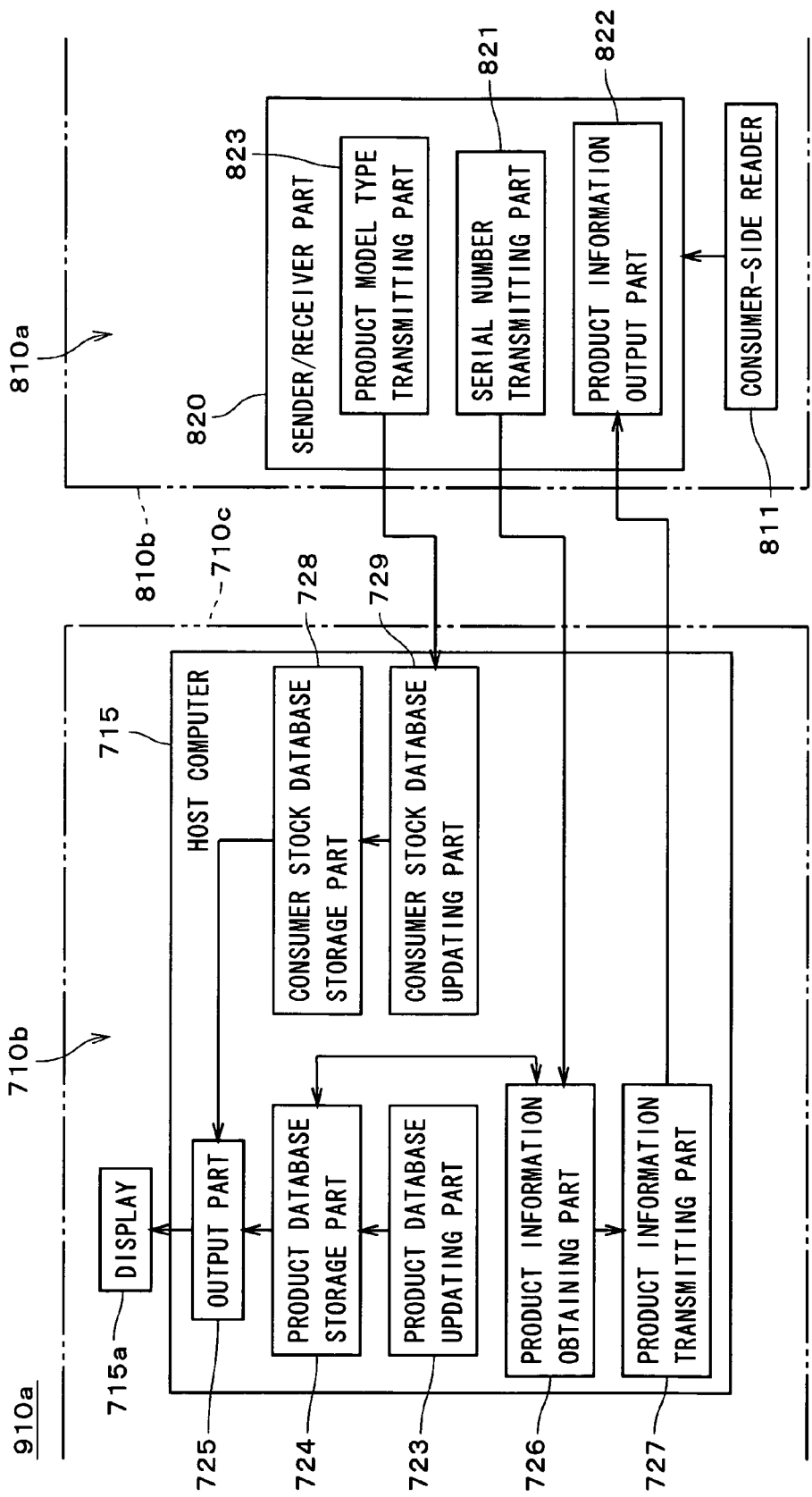
FIG. 28 is a block diagram showing some of functions of the diaper product management system.

Next, another diaper product management system 910*a* will be discussed. FIG. 28 is a block diagram showing some of functions of the diaper product management system 910*a*. The diaper product management system 910*a*, like the diaper product management system 910 of FIG. 19, comprises a supply information management system 710*b* which is managed on the supplier side of the diaper products and a usage information management system 810*a* which is managed on the consumer side of the diaper products and connected with the supply information management system 710*b* by the communication network 911 (see FIG. 19). The functions surrounded by the two-dot chain line 710*c* of FIG. 28 are some of the functions of the supply information management system 710*b* and the functions surrounded by the two-dot chain line 810*b* are some of the functions of the usage information management system 810*a*.

The supply information management system 710*b* is the same as the above-discussed supply information management system 710*a* in function except that it further has a consumer stock database storage part 728 and a consumer stock database updating part 729 as functions implemented by the CPU, the memories and the like in the host computer 715. The usage information management system 810*a* is the same as the above-discussed usage information management system 810 in function except that the sender/receiver part 820 further has a product model type transmitting part 823 as a function implemented by the CPU, the memories and the like in the management device 812 (see FIG. 19).

The consumer stock database storage part 728 stores a consumer stock database 97 shown in FIG. 29. As shown in FIG. 29, the consumer stock database 97 is a set of data elements each associating a facility identification number specifying the consumer-side facility and a plurality of product model types of the diaper products with the stock number for the diaper product corresponding to each of the product model types in the consumer-side facility. The consumer stock database updating part 729 updates the consumer stock database 97 every time when the diaper product is put on the wearer in the consumer-side facility. The product model type transmitting part 823 transmits the product model type of the diaper product which is read out by the consumer-side reader 811 to the host computer 715 in the supply information management system 710*b* through the communication network 911 (see FIG. 19).

In the consumer-side facility, when a caregiver puts the diaper product on a wearer, the product model type of the diaper product to be put on are read out by the consumer-side reader 811 and transmitted to the sender/receiver part 820, and the product model type transmitting part 823 transmits the product model type together with the facility identification number specifying the consumer-side facility to the host computer 715 in the supply information management system 710*b*.

In the supply information management system 710*b*, the consumer stock database updating part 729 receives the facility identification number and the product model type from the product model type transmitting part 823 and specifies the data element including these facility identification number and the product model type in the consumer stock database 97 stored in the consumer stock database storage part 728. Then, the consumer stock database updating part 729 subtracts 1 from the value of the stock number in the specified data element.

Thus, in the diaper product management system 910*a*, the supplier side of the diaper products can accurately keep track of the stock number for the diaper product in each consumer-side facility. Since the supplier can forecast the number of diaper products which should be prepared for each consumer-side facility at this point of time with high accuracy, the stock of diaper products on the supplier side can be compressed. Further, it is possible to make a sales offer at good timing when the stock number for the diaper product decreases in each consumer-side facility.

The individual functions in the above-discussed supply information management system and usage information management system are not necessarily implemented by software but may be partially or entirely implemented by special hardware. Each of these systems is not necessarily located at one place as one system but may be implemented by cooperation of computer systems which are separately located as necessary.

Each of the above-discussed databases is not necessarily stored individually in one storage part but a plurality of databases may be mixedly stored in one storage part, or a plurality of databases may be processed substantially as one data set. Conversely, one database may be divided and stored separately in a plurality of storage parts. The respective data structures of the above-discussed databases are only exemplary ones and may be changed as appropriate only if the like effects can be produced.

While the invention has been shown and described in detail, the foregoing description is in all aspects illustrative and not restrictive. It is therefore understood that numerous modifications and variations can be devised without departing from the scope of the invention.

The invention claimed is:

1. A diaper product comprising:
a disposable diaper;
an auxiliary absorbent pad attached inside said disposable diaper, for receiving excrement from a wearer;
a first IC tag having a first IC chip and a first antenna for radio communication connected to said first IC chip, said first IC tag being attached to said disposable diaper; and
a second IC tag having a second IC chip and a second antenna for radio communication connected to said second IC chip, said second IC tag being attached to said auxiliary absorbent pad,
wherein a serial number for discriminating said disposable diaper from other disposable diapers is stored in said first IC chip and can be read out through said first antenna, and
wherein a serial number for discriminating said auxiliary absorbent pad from other auxiliary absorbent pads is stored in said second IC chip and can be read out through said second antenna.

2. A supply information management system for managing information on supply of diaper products, comprising:
a writing device provided in a station where a predetermined process of at least one of manufacturing, inspecting, storing, shipping and selling on supply of a diaper product is performed, said writing device being provided for writing to store process information on said predetermined process to an IC chip of an IC tag attached to said diaper product through an antenna of said IC tag for radio communication;
a reading device for reading a process information together with a serial number stored in an IC chip;
a product database storage part for storing a product database which is a set of data elements each associating a serial number with process information; and
a product database updating part for specifying a data element in said product database, which includes a serial number read out by said reading device, and adding process information read out by said reading device to said data element.

3. The supply information management system according to claim 2, further comprising:
a confirming part for confirming whether process information read out by said reading device between a first process included in said predetermined process and a second process after said first process includes first process information written to said IC chip by said writing device in said first process; and
a transmitting part for transmitting a serial number and first process information which are read out by said reading device to said product database updating part in a case where process information confirmed by said confirming part includes said first process information.

4. The supply information management system according to claim 2, further comprising:
a portable reading device for reading a serial number and process information stored in an IC chip of an IC tag attached to a diaper product in a noncontact manner and outputting said serial number and said process information.

5. The supply information management system according to claim 4, wherein said serial number and said process information which are read out by said reading device and/or said portable reading device are transmitted to said product database updating part through internet.

6. The supply information management system according to claim 2, wherein said station includes at least one of a manufacturing station for performing a process of manufacturing a diaper product, an inspection station for performing a process of inspecting a diaper product, a storage station for performing a process of storing or retrieving a diaper product, a shipping station for performing a process of shipping a diaper product and a sales station for performing a process of selling a diaper product.

7. The supply information management system according to claim 6, wherein said station includes said manufacturing station, and
wherein said writing device provided in said manufacturing station writes at least one of a product model type indicating a kind of said diaper product and its manufacturing date and time to said IC chip as said process information.

8. The supply information management system according to claim 6, wherein said station includes said inspection station, and
wherein said writing device provided in said inspection station writes at least one of inspecting date and time of said diaper product, an inspector name and an inspecting device to said IC chip as said process information.

9. The supply information management system according to claim 6, wherein said station includes said storage station, and
wherein said writing device provided in said storage station writes at least one of storing date and time and retrieving date and time of said diaper product to said IC chip as said process information.

10. The supply information management system according to claim 6, wherein said station includes said shipping station, and
wherein said writing device provided in said shipping station writes at least one of shipping date and time and a destination of said diaper product to said IC chip as said process information.

11. The supply information management system according to claim 6, wherein said station includes said sales station, and
wherein said writing device provided in said sales station writes selling date and time of said diaper product to said IC chip as said process information.

12. A supply information management system for managing information on supply of diaper products, comprising:
a reading device for reading a serial number stored in an IC chip of an IC tag attached to a diaper product through an antenna of said IC tag for radio communication;
a product database storage part for storing a product database which is a set of data elements each associating a serial number of a diaper product with process information on a predetermined process of at least one of manufacturing, inspecting, storing, shipping and selling on supply of said diaper product; and a product database updating part for specifying a data element in said product database, which includes a serial number read out by said reading device, and adding process information on a process for a diaper product to said data element when said process is performed.

13. A usage information management system for managing information on usage of diaper products, comprising:
   a reading device for reading a product model type indicating a kind of diaper product and a serial number which are stored in advance in an IC chip of an IC tag attached to said diaper product through an antenna of said IC tag for radio communication;
   a stock database storage part for storing a stock database which is a set of data elements each associating a serial number of a diaper product with a product model type and a state of usage of said diaper product;
   a stock database updating part for specifying a data element in said stock database, which includes a serial number read out by said reading device, and updating a value of a data item in said data element which indicates a state of usage from a value of "unused" to that of "used" when said diaper product is put on a wearer; and
   a stock number obtaining part for specifying data elements in said stock database, each of which includes one product model type out of a plurality of product model types and a data item indicating said state of usage which has a value of "unused", and obtaining the number of said data elements as a stock number for a diaper product corresponding to said product model type.

14. The usage information management system according to claim 13, further comprising:
   an order condition storage part for storing a stock threshold value and the number of reordered products corresponding to each of said plurality of product model types; and
   a reorder part for transmitting a product model type and order information indicating the number of reordered products for said product model type to a selling agency through a communication network when a stock number for a diaper product corresponding to said product model type, which is obtained by said stock number obtaining part, falls short of a stock threshold value of said product model type.

15. A usage information management system for managing information on usage of diaper products, comprising:
   a first reading device for reading a product model type indicating a kind of diaper product, which is stored in an IC chip of an IC tag attached to a diaper product through an antenna of said IC tag for radio communication;
   a second reading device for reading a wearer identification number for discriminating one wearer of a diaper product from other wearers;
   a wearer database storage part for storing a wearer database which is a set of data elements each associating a wearer identification number with an applicable model type which is a product model type of a diaper product to be put on a wearer corresponding to said wearer identification number;
   a model type check part for specifying a data element in said wearer database, which includes a wearer identification number read out by said second reading device, and checking an applicable model type in said data element with a product model type read out by said first reading device; and
   a wearer database updating part for specifying a data element in said wearer database, which includes a wearer identification number read out by said second reading device, and updating a value of applicable model type in said data element to a product model type read out from a diaper product by said first reading device when a change of applicable model type of a diaper product to be put on a wearer is needed.

16. A usage information management system for managing information on usage of diaper products, comprising:
   a first reading device for reading a product model type indicating a kind of diaper product, which is stored in an IC chip of an IC tag attached to a diaper product through an antenna of said IC tag for radio communication;
   a second reading device for reading a wearer identification number for discriminating one wearer of a diaper product from other wearers;
   a wearer database storage part for storing a wearer database which is a set of data elements each associating a wearer identification number with an applicable model type which is a product model type of a diaper product to be put on a wearer corresponding to said wearer identification number; and
   a model type check part for specifying a data element in said wearer database, which includes a wearer identification number read out by said second reading device, and checking an applicable model type in said data element with a product model type read out by said first reading device,
   wherein a data element of said wearer database includes latest wearing date and time associated with a wearer identification number, and
   when one diaper product is put on a wearer, said wearer database updating part specifies a data element in said wearer database, which includes a wearer identification number read out by said second reading device, and updates latest wearing date and time in said data element.

17. The usage information management system according to claim 16, further comprising a change-scheduled date and time output part for outputting next change-scheduled date and time for each wearer on the basis of a wearer identification number, latest wearing date and time and a change interval included in a data element corresponding to said each wearer.

18. The usage information management system according to claim 17, wherein a data element of said wearer database includes a plurality of latest wearing dates and times and a plurality of change intervals corresponding to a plurality of product model types of diaper products associated with a wearer identification number, and
   wherein said change-scheduled date and time output part outputs a next change-scheduled date and time on the basis of latest wearing date and time and a change interval of a data element including a wearer identification number read out by said second reading device and a product model type of a diaper product read out by said first reading device when said diaper product is put on a wearer.

19. A usage information management system for managing information on usage of diaper products, comprising:
   a first reading device for reading a product model type indicating a kind of diaper product, which is stored in an IC chip of an IC tag attached to a diaper product through an antenna of said IC tag for radio communication;
   a second reading device for reading a wearer identification number for discriminating one wearer of a diaper product from other wearers;
   a wearer database storage part for storing a wearer database which is a set of data elements each associating a wearer identification number with an applicable model type which is a product model type of a diaper product to be put on a wearer corresponding to said wearer identification number;
a model type check part for specifying a data element in said wearer database, which includes a wearer identification number read out by said second reading device, and checking an applicable model type in said data element with a product model type read out by said first reading device;
a wearing date and time database storage part for storing a wearing date and time database which is a set of data elements each associating a product model type of a diaper product and a wearer identification number with wearing date and time when said product model type of said diaper product is put on a wearer corresponding to said wearer identification number;
a wearing date and time database updating part for adding a new data element to said wearing date and time database when one diaper product is put on a wearer, said new data element including a product model type of said diaper product, which is read out by said first reading device, a wearer identification number read out by said second reading device and wearing date and time of said diaper product; and
a usage frequency obtaining part for specifying a plurality of data elements having the same product model type and wearer identification number in said wearing date and time database and obtaining a usage frequency indicating the number of used diaper products in a predetermined period on the basis of wearing dates and times of said plurality of data elements.

20. The usage information management system according to claim 19, wherein a plurality of data elements in said wearing date and time database include product model types corresponding to disposable diapers and other plurality of data elements include product model types corresponding to auxiliary absorbent pads attached inside said disposable diapers.

21. A usage information management system for managing information on usage of diaper products, comprising:
a first reading device for reading a product model type indicating a kind of diaper product, which is stored in an IC chip of an IC tag attached to a diaper product through an antenna of said IC tag for radio communication;
a second reading device for reading a wearer identification number for discriminating one wearer of a diaper product from other wearers;
a wearer database storage part for storing a wearer database which is a set of data elements each associating a wearer identification number with an applicable model type which is a product model type of a diaper product to be put on a wearer corresponding to said wearer identification number;
a model type check part for specifying a data element in said wearer database, which includes a wearer identification number read out by said second reading device, and checking an applicable model type in said data element with a product model type read out by said first reading device;
a price database storage part for storing a price database which is a set of data elements each associating a product model type of a diaper product with its price;
a billing database storage part for storing a billing database which is a set of data elements each associating a wearer identification number with a billing amount for cost on usage of a diaper product; and
a billing database updating part for specifying a data element in said price database, which includes a product model type of a diaper product, which is read out by said first reading device, to acquire a price of said diaper product and specifying a data element in said billing database, which includes a wearer identification number read out by said second reading device, and updating a billing amount of a data element including said wearer identification number to a sum obtained by adding said price of said diaper product to said billing amount when said diaper product is put on a wearer.

22. A usage information management system for managing information on usage of diaper products, comprising:
a first reading device for reading a product model type indicating a kind of diaper product, which is stored in an IC chip of an IC tag attached to a diaper product through an antenna of said IC tag for radio communication;
a second reading device for reading a wearer identification number for discriminating one wearer of a diaper product from other wearers;
a wearer database storage part for storing a wearer database which is a set of data elements each associating a wearer identification number with an applicable model type which is a product model type of a diaper product to be put on a wearer corresponding to said wearer identification number;
a model type check part for specifying a data element in said wearer database, which includes a wearer identification number read out by said second reading device, and checking an applicable model type in said data element with a product model type read out by said first reading device;
a price database storage part for storing a price database which is a set of data elements each associating a product model type of a diaper product with its price;
a billing database storage part for storing a billing database which is a set of data elements each associating a wearer identification number with a self-pay ratio and a billing amount for cost on use of a diaper product; and
a billing database updating part for specifying a data element in said price database, which includes a product model type of a diaper product, which is read out by said first reading device, to acquire a price of said diaper product and specifying a data element in said billing database, which includes a wearer identification number read out by said second reading device and updating a billing amount of a data element including said wearer identification number to a sum obtained by adding a product of said price of said diaper product and said self-pay ratio to said billing amount when said diaper product is put on a wearer.

23. A diaper product management system for managing information on diaper products, comprising:
a supply information management system managed on a supplier side, where diaper products are manufactured and sold, for managing information on supply of diaper products; and
a usage information management system managed on a consumer side, where diaper products are consumed and connected to said supply information management system through a communication network, for managing information on usage of diaper products,
wherein said supply information management system comprises (i) supplier-side reading device for reading a serial number stored in an IC chip of an IC tag attached to a diaper product through an antenna of said IC tag for radio communication;

(ii) a product database storage part for storing a product database which is a set of data elements each associating a serial number of a diaper product with process information on a predetermined process of at least one of manufacturing, inspecting, storing, shipping and selling on supply of said diaper product;

(iii) a product database updating part for specifying a data element in said product database, which includes a serial number read out by said supplier-side reading device, and adding process information on said process to said data element;

(iv) a product information obtaining part for specifying a data element in said product database, which includes a serial number transmitted from said usage information management system to acquire a value of a predetermined data item in said data element as product information; and (v) a product information transmitting part for transmitting product information acquired by said product information obtaining part to said usage information management system through said communication network, and wherein said usage information management system comprises (i) a consumer-side reading device for reading a serial number stored in an IC chip of an IC tag attached to a diaper product;

(ii) a serial number transmitting part for transmitting a serial number read out by said consumer-side reading device to said supply information management system through said communication network; and (iii) a product information output part for receiving and outputting product information transmitted by said product information transmitting part of said supply information management system.

24. The diaper product management system according to claim 23, wherein said usage information management system further comprises a product model type transmitting part for transmitting a product model type indicating a kind of a diaper product, which is stored in an IC chip of an IC tag attached to said diaper product and read out by said consumer-side reading device, to said supply information management system when said diaper product is put on a wearer, and wherein said supply information management system further comprises a stock database storage part for storing a stock database which is a set of data elements associating a plurality of product model types of diaper products with respective stock numbers of diaper products on said consumer side corresponding to said plurality of product model types; and a stock database updating part for specifying a data element in said stock database, which includes a product model type transmitted from said product model type transmitting part, and subtracting one from a stock number in said data element.

* * * * *